(12) United States Patent
Stahmann et al.

(10) Patent No.: US 9,592,391 B2
(45) Date of Patent: Mar. 14, 2017

(54) SYSTEMS AND METHODS FOR DETECTING CARDIAC ARRHYTHMIAS

(71) Applicant: Cardiac Pacemakers, Inc., St. Paul, MN (US)

(72) Inventors: Jeffrey E. Stahmann, Ramsey, MN (US); Howard D. Simms, Jr., Shoreview, MN (US); Keith R. Maile, New Brighton, MN (US); Michael J. Kane, Roseville, MN (US); William J. Linder, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/592,698

(22) Filed: Jan. 8, 2015

(65) Prior Publication Data

US 2015/0196758 A1    Jul. 16, 2015

Related U.S. Application Data

(60) Provisional application No. 61/926,051, filed on Jan. 10, 2014.

(51) Int. Cl.
| | |
|---|---|
| *A61N 1/362* | (2006.01) |
| *A61N 1/372* | (2006.01) |
| *A61N 1/39* | (2006.01) |
| *A61N 1/375* | (2006.01) |

(Continued)

(52) U.S. Cl.
CPC .......... *A61N 1/3622* (2013.01); *A61B 5/0464* (2013.01); *A61N 1/3621* (2013.01); *A61N 1/3756* (2013.01); *A61N 1/37288* (2013.01); *A61N 1/3956* (2013.01); *A61N 1/3962* (2013.01); *A61B 5/0006* (2013.01); *A61B 5/0031* (2013.01); *A61B 5/4836* (2013.01); *A61B 5/686* (2013.01)

(58) Field of Classification Search
None
See application file for complete search history.

(56) References Cited

U.S. PATENT DOCUMENTS

| | | |
|---|---|---|
| 3,835,864 A | 9/1974 | Rasor et al. |
| 3,943,936 A | 3/1976 | Rasor et al. |
| 4,142,530 A | 3/1979 | Wittkampf |

(Continued)

FOREIGN PATENT DOCUMENTS

| | | |
|---|---|---|
| AU | 2008279789 B2 | 10/2011 |
| AU | 2008329620 B2 | 5/2014 |

(Continued)

OTHER PUBLICATIONS

US 8,886,318, 11/2014, Jacobson et al. (withdrawn)

(Continued)

*Primary Examiner* — Brian T Gedeon
(74) *Attorney, Agent, or Firm* — Seager, Tufte & Wickhem, LLP.

(57) ABSTRACT

Systems and methods for coordinating detection and/or treatment of abnormal heart activity using multiple implanted devices within a patient. In one example, cardiac activity may be sensed by two or more medical device, including a leadless cardiac pacemaker. Cardiac activity sensed by one of the implanted devices may be communicated to another one of the implanted devices. Abnormal heart activity may then be determined based on the cardiac activity of both of the medical device.

20 Claims, 23 Drawing Sheets

(51) Int. Cl.
*A61B 5/0464* (2006.01)
*A61B 5/00* (2006.01)

(56) References Cited

U.S. PATENT DOCUMENTS

| | | |
|---|---|---|
| 4,151,513 A | 4/1979 | Menken et al. |
| 4,157,720 A | 6/1979 | Greatbatch |
| RE30,366 E | 8/1980 | Rasor et al. |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,333,470 A | 6/1982 | Barthel |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,531,527 A | 7/1985 | Reinhold, Jr. et al. |
| 4,539,999 A | 9/1985 | Mans |
| 4,556,063 A | 12/1985 | Thompson et al. |
| 4,562,841 A | 1/1986 | Brockway et al. |
| 4,585,004 A | 4/1986 | Brownlee |
| 4,589,420 A | 5/1986 | Adams et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| RE32,378 E | 3/1987 | Barthel |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,884,345 A | 12/1989 | Long |
| 4,886,064 A | 12/1989 | Strandberg |
| 4,924,875 A | 5/1990 | Chamoun |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,000,189 A | 3/1991 | Throne et al. |
| 5,002,052 A | 3/1991 | Haluska |
| 5,012,806 A | 5/1991 | De Bellis |
| 5,014,698 A | 5/1991 | Cohen |
| 5,036,849 A | 8/1991 | Hauck et al. |
| 5,058,581 A | 10/1991 | Silvian |
| 5,078,134 A | 1/1992 | Heilman et al. |
| 5,107,850 A | 4/1992 | Olive |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,139,028 A | 8/1992 | Steinhaus et al. |
| 5,144,950 A | 9/1992 | Stoop et al. |
| 5,156,148 A | 10/1992 | Cohen |
| 5,161,527 A | 11/1992 | Nappholz et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,193,550 A | 3/1993 | Duffin |
| 5,205,283 A | 4/1993 | Olson |
| 5,215,098 A | 6/1993 | Steinhaus et al. |
| 5,217,021 A | 6/1993 | Steinhaus et al. |
| 5,241,961 A | 9/1993 | Henry |
| 5,243,977 A | 9/1993 | Trabucco et al. |
| 5,255,186 A | 10/1993 | Steinhaus et al. |
| 5,265,602 A | 11/1993 | Anderson et al. |
| 5,269,326 A | 12/1993 | Verrier |
| 5,271,411 A | 12/1993 | Ripley et al. |
| 5,273,049 A | 12/1993 | Steinhaus et al. |
| 5,275,621 A | 1/1994 | Mehra |
| 5,284,136 A | 2/1994 | Hauck et al. |
| 5,292,348 A | 3/1994 | Saumarez et al. |
| 5,300,107 A | 4/1994 | Stokes et al. |
| 5,301,677 A | 4/1994 | Hsung |
| 5,312,439 A | 5/1994 | Loeb |
| 5,312,445 A | 5/1994 | Nappholz et al. |
| 5,313,953 A | 5/1994 | Yomtov et al. |
| 5,314,459 A | 5/1994 | Swanson et al. |
| 5,318,597 A | 6/1994 | Hauck et al. |
| 5,324,310 A | 6/1994 | Greeninger et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,360,436 A | 11/1994 | Alt et al. |
| 5,366,487 A | 11/1994 | Adams et al. |
| 5,372,606 A | 12/1994 | Lang et al. |
| 5,376,106 A | 12/1994 | Stahmann et al. |
| 5,378,775 A | 1/1995 | Shimizu et al. |
| 5,379,775 A | 1/1995 | Kruse |
| 5,379,776 A | 1/1995 | Murphy et al. |
| 5,383,915 A | 1/1995 | Adams |
| 5,388,578 A | 2/1995 | Yomtov et al. |
| 5,400,795 A | 3/1995 | Murphy et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,447,524 A | 9/1995 | Alt |
| 5,448,997 A | 9/1995 | Kruse et al. |
| 5,456,261 A | 10/1995 | Luczyk |
| 5,456,691 A | 10/1995 | Snell |
| 5,458,623 A | 10/1995 | Lu et al. |
| 5,466,246 A | 11/1995 | Silvian |
| 5,468,254 A | 11/1995 | Hahn et al. |
| 5,503,160 A | 4/1996 | Pering et al. |
| 5,509,927 A | 4/1996 | Epstein et al. |
| 5,520,191 A | 5/1996 | Karlsson et al. |
| 5,522,866 A | 6/1996 | Fernald |
| 5,531,767 A | 7/1996 | Fain |
| 5,540,727 A | 7/1996 | Tockman et al. |
| 5,545,186 A | 8/1996 | Olson et al. |
| 5,545,202 A | 8/1996 | Dahl et al. |
| 5,591,214 A | 1/1997 | Lu |
| 5,620,466 A | 4/1997 | Haefner et al. |
| 5,620,471 A | 4/1997 | Duncan |
| 5,630,425 A | 5/1997 | Panescu et al. |
| 5,634,468 A | 6/1997 | Platt et al. |
| 5,634,938 A | 6/1997 | Swanson et al. |
| 5,645,070 A | 7/1997 | Turcott |
| 5,662,688 A | 9/1997 | Haefner et al. |
| 5,674,259 A | 10/1997 | Gray |
| 5,682,900 A | 11/1997 | Arand et al. |
| 5,683,425 A | 11/1997 | Hauptmann |
| 5,683,426 A | 11/1997 | Greenhut et al. |
| 5,683,432 A | 11/1997 | Goedeke et al. |
| 5,712,801 A | 1/1998 | Turcott |
| 5,713,367 A | 2/1998 | Arnold et al. |
| 5,720,770 A | 2/1998 | Nappholz et al. |
| 5,728,154 A | 3/1998 | Crossett et al. |
| 5,738,105 A | 4/1998 | Kroll |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,766,225 A | 6/1998 | Kramm |
| 5,774,501 A | 6/1998 | Halpern et al. |
| 5,776,168 A | 7/1998 | Gunderson |
| 5,779,645 A | 7/1998 | Olson et al. |
| 5,792,065 A | 8/1998 | Xue et al. |

(56) References Cited

U.S. PATENT DOCUMENTS

| | | |
|---|---|---|
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,795,303 A | 8/1998 | Swanson et al. |
| 5,814,089 A | 9/1998 | Stokes et al. |
| 5,817,133 A | 10/1998 | Houben |
| 5,819,741 A | 10/1998 | Karlsson et al. |
| 5,827,197 A | 10/1998 | Bocek et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,848,972 A | 12/1998 | Triedman et al. |
| 5,855,593 A | 1/1999 | Olson et al. |
| 5,857,977 A | 1/1999 | Caswell et al. |
| 5,873,894 A | 2/1999 | Vandegriff et al. |
| 5,873,897 A | 2/1999 | Armstrong et al. |
| 5,891,170 A | 4/1999 | Nitzsche et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,935,081 A | 8/1999 | Kadhiresan |
| 5,941,906 A | 8/1999 | Barreras et al. |
| 5,954,662 A | 9/1999 | Swanson et al. |
| 5,954,757 A | 9/1999 | Gray |
| 5,978,707 A | 11/1999 | Krig et al. |
| 5,978,713 A | 11/1999 | Prutchi et al. |
| 5,991,660 A | 11/1999 | Goyal |
| 5,999,848 A | 12/1999 | Gord et al. |
| 5,999,857 A | 12/1999 | Weijand et al. |
| 6,026,320 A | 2/2000 | Carlson et al. |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,080,187 A | 6/2000 | Alt et al. |
| 6,083,248 A | 7/2000 | Thompson |
| 6,106,551 A | 8/2000 | Crossett et al. |
| 6,108,578 A | 8/2000 | Bardy et al. |
| 6,115,636 A | 9/2000 | Ryan |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,151,524 A | 11/2000 | Krig et al. |
| 6,162,195 A | 12/2000 | Igo et al. |
| 6,164,284 A | 12/2000 | Schulman et al. |
| 6,167,310 A | 12/2000 | Grevious |
| 6,169,918 B1 | 1/2001 | Haefner et al. |
| 6,178,350 B1 | 1/2001 | Olson et al. |
| 6,179,865 B1 | 1/2001 | Hsu et al. |
| 6,208,894 B1 | 3/2001 | Schulman et al. |
| 6,211,799 B1 | 4/2001 | Post et al. |
| 6,212,428 B1 | 4/2001 | Hsu et al. |
| 6,221,011 B1 | 4/2001 | Bardy |
| 6,223,078 B1 | 4/2001 | Marcovecchio |
| 6,230,055 B1 | 5/2001 | Sun et al. |
| 6,230,059 B1 | 5/2001 | Duffin |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,554 B1 | 7/2001 | Hsu et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,275,732 B1 | 8/2001 | Hsu et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,298,271 B1 | 10/2001 | Weijand |
| 6,308,095 B1 | 10/2001 | Hsu et al. |
| 6,312,378 B1 | 11/2001 | Bardy |
| 6,312,388 B1 | 11/2001 | Marcovecchio et al. |
| 6,315,721 B2 | 11/2001 | Schulman et al. |
| 6,317,632 B1 | 11/2001 | Krig et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,405,083 B1 | 6/2002 | Rockwell et al. |
| 6,409,674 B1 | 6/2002 | Brockway et al. |
| 6,411,848 B2 | 6/2002 | Kramer et al. |
| 6,424,865 B1 | 7/2002 | Ding |
| 6,430,435 B1 | 8/2002 | Hsu et al. |
| 6,434,417 B1 | 8/2002 | Lovett |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,449,503 B1 | 9/2002 | Hsu |
| 6,453,200 B1 | 9/2002 | Koslar |
| 6,456,871 B1 | 9/2002 | Hsu et al. |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,477,404 B1 | 11/2002 | Yonce et al. |
| 6,480,733 B1 | 11/2002 | Turcott |
| 6,480,745 B2 | 11/2002 | Nelson et al. |
| 6,484,055 B1 | 11/2002 | Marcovecchio |
| 6,487,443 B2 | 11/2002 | Olson et al. |
| 6,490,487 B1 | 12/2002 | Kraus et al. |
| 6,493,579 B1 | 12/2002 | Gilkerson et al. |
| 6,505,067 B1 | 1/2003 | Lee et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,522,917 B1 | 2/2003 | Hsu et al. |
| 6,522,925 B1 | 2/2003 | Gilkerson et al. |
| 6,526,311 B2 | 2/2003 | Begemann |
| 6,526,313 B2 | 2/2003 | Sweeney et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,352 B2 | 6/2003 | Combs et al. |
| 6,597,948 B1 | 7/2003 | Rockwell et al. |
| 6,597,951 B2 | 7/2003 | Kadhiresan et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,658,283 B1 | 12/2003 | Bornzin et al. |
| 6,658,286 B2 | 12/2003 | Seim |
| 6,666,844 B1 | 12/2003 | Igo et al. |
| 6,671,548 B1 | 12/2003 | Mouchawar et al. |
| 6,687,540 B2 | 2/2004 | Marcovecchio |
| 6,689,117 B2 | 2/2004 | Sweeney et al. |
| 6,690,959 B2 | 2/2004 | Thompson |
| 6,704,602 B2 | 3/2004 | Berg et al. |
| 6,708,058 B2 | 3/2004 | Kim et al. |

(56) References Cited

U.S. PATENT DOCUMENTS

| | | |
|---|---|---|
| 6,718,212 B2 | 4/2004 | Parry et al. |
| 6,721,597 B1 | 4/2004 | Bardy et al. |
| 6,728,572 B2 | 4/2004 | Hsu et al. |
| 6,738,670 B1 | 5/2004 | Almendinger et al. |
| 6,745,068 B2 | 6/2004 | Koyrakh et al. |
| 6,749,566 B2 | 6/2004 | Russ |
| 6,758,810 B2 | 7/2004 | Lebel et al. |
| 6,760,615 B2 | 7/2004 | Ferek-Petric |
| 6,763,269 B2 | 7/2004 | Cox |
| 6,766,190 B2 | 7/2004 | Ferek-Petric |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,889,081 B2 | 5/2005 | Hsu |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,959,212 B2 | 10/2005 | Hsu et al. |
| 6,978,176 B2 | 12/2005 | Lattouf |
| 6,978,177 B1 | 12/2005 | Chen et al. |
| 6,985,773 B2 | 1/2006 | Von Arx et al. |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,031,764 B2 | 4/2006 | Schwartz et al. |
| 7,039,463 B2 | 5/2006 | Marcovecchio |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,110,824 B2 | 9/2006 | Amundson et al. |
| 7,120,504 B2 | 10/2006 | Osypka |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,203,535 B1 | 4/2007 | Hsu et al. |
| 7,206,423 B1 | 4/2007 | Feng et al. |
| 7,209,790 B2 | 4/2007 | Thompson et al. |
| 7,212,871 B1 | 5/2007 | Morgan |
| 7,226,440 B2 | 6/2007 | Gelfand et al. |
| 7,228,176 B2 | 6/2007 | Smith et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,956 B2 | 4/2009 | Thompson |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,751,890 B2 | 7/2010 | McCabe et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |

(56) References Cited

U.S. PATENT DOCUMENTS

| | | |
|---|---|---|
| 7,809,438 B2 | 10/2010 | Echt et al. |
| 7,840,281 B2 | 11/2010 | Kveen et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | HüBinette |
| 7,949,404 B2 | 5/2011 | Hill |
| 7,949,405 B2 | 5/2011 | Feher |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,233,985 B2 | 7/2012 | Bulkes et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,527,068 B2 | 9/2013 | Ostroff |
| 8,532,790 B2 | 9/2013 | Griswold |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |

(56) References Cited

U.S. PATENT DOCUMENTS

| | | |
|---|---|---|
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | Dal Molin et al. |
| 8,718,773 B2 | 5/2014 | Willis et al. |
| 8,738,147 B2 | 5/2014 | Hastings et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,500 B2 | 12/2014 | Smith et al. |
| 8,903,513 B2 | 12/2014 | Ollivier |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 2002/0002389 A1 | 1/2002 | Bradley et al. |
| 2002/0032469 A1 | 3/2002 | Marcovecchio |
| 2002/0032470 A1 | 3/2002 | Linberg |
| 2002/0035335 A1 | 3/2002 | Schauerte |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049474 A1 | 4/2002 | Marcovecchio et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0072778 A1 | 6/2002 | Guck et al. |
| 2002/0082665 A1 | 6/2002 | Haller et al. |
| 2002/0087091 A1 | 7/2002 | Koyrakh et al. |
| 2002/0091333 A1 | 7/2002 | Hsu et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107552 A1 | 8/2002 | Krig et al. |
| 2002/0107559 A1 | 8/2002 | Sanders et al. |
| 2002/0120299 A1 | 8/2002 | Ostroff et al. |
| 2002/0123768 A1 | 9/2002 | Gilkerson et al. |
| 2002/0123769 A1 | 9/2002 | Panken et al. |
| 2002/0143370 A1 | 10/2002 | Kim |
| 2002/0147407 A1 | 10/2002 | Seim |
| 2002/0147474 A1 | 10/2002 | Seim et al. |
| 2002/0173830 A1 | 11/2002 | Starkweather et al. |
| 2002/0183637 A1 | 12/2002 | Kim et al. |
| 2002/0183639 A1 | 12/2002 | Sweeney et al. |
| 2002/0193846 A1 | 12/2002 | Pool et al. |
| 2002/0198461 A1 | 12/2002 | Hsu et al. |
| 2003/0004552 A1 | 1/2003 | Plombon et al. |
| 2003/0009203 A1 | 1/2003 | Lebel et al. |
| 2003/0028082 A1 | 2/2003 | Thompson |
| 2003/0041866 A1 | 3/2003 | Linberg et al. |
| 2003/0050563 A1 | 3/2003 | Suribhotla et al. |
| 2003/0060849 A1 | 3/2003 | Hsu |
| 2003/0069609 A1 | 4/2003 | Thompson |
| 2003/0083586 A1 | 5/2003 | Ferek-Petric |
| 2003/0083587 A1 | 5/2003 | Ferek-Petric |
| 2003/0088278 A1 | 5/2003 | Bardy et al. |
| 2003/0097153 A1 | 5/2003 | Bardy et al. |
| 2003/0100923 A1 | 5/2003 | Bjorling et al. |
| 2003/0105491 A1 | 6/2003 | Gilkerson et al. |
| 2003/0109792 A1 | 6/2003 | Hsu et al. |
| 2003/0114889 A1 | 6/2003 | Huvelle et al. |
| 2003/0114908 A1 | 6/2003 | Flach |
| 2003/0120316 A1 | 6/2003 | Spinelli et al. |
| 2003/0144701 A1 | 7/2003 | Mehra et al. |
| 2003/0181818 A1 | 9/2003 | Kim et al. |
| 2003/0187460 A1 | 10/2003 | Chin et al. |
| 2003/0187461 A1 | 10/2003 | Chin |
| 2003/0208238 A1 | 11/2003 | Weinberg et al. |
| 2004/0015090 A1 | 1/2004 | Sweeney et al. |
| 2004/0024435 A1 | 2/2004 | Leckrone et al. |
| 2004/0087938 A1 | 5/2004 | Leckrone et al. |
| 2004/0088035 A1 | 5/2004 | Guenst et al. |
| 2004/0093035 A1 | 5/2004 | Schwartz et al. |
| 2004/0102830 A1 | 5/2004 | Williams |

(56) References Cited

U.S. PATENT DOCUMENTS

| | | |
|---|---|---|
| 2004/0116820 A1 | 6/2004 | Daum et al. |
| 2004/0116972 A1 | 6/2004 | Marcovecchio |
| 2004/0127806 A1 | 7/2004 | Sweeney et al. |
| 2004/0127959 A1 | 7/2004 | Amundson et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176694 A1 | 9/2004 | Kim et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0267303 A1 | 12/2004 | Guenst |
| 2005/0010257 A1 | 1/2005 | Lincoln et al. |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149134 A1 | 7/2005 | McCabe et al. |
| 2005/0149135 A1 | 7/2005 | Krig et al. |
| 2005/0149138 A1 | 7/2005 | Min et al. |
| 2005/0159781 A1 | 7/2005 | Hsu |
| 2005/0165466 A1 | 7/2005 | Morris et al. |
| 2005/0182465 A1 | 8/2005 | Ness |
| 2005/0197674 A1 | 9/2005 | McCabe et al. |
| 2005/0203410 A1 | 9/2005 | Jenkins |
| 2005/0256544 A1 | 11/2005 | Thompson |
| 2005/0283208 A1 | 12/2005 | Von Arx et al. |
| 2006/0015148 A1 | 1/2006 | McCabe et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0074330 A1 | 4/2006 | Smith et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0122527 A1 | 6/2006 | Marcovecchio |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2006/0281998 A1 | 12/2006 | Li |
| 2007/0004979 A1 | 1/2007 | Wojciechowicz et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |

(56) References Cited

U.S. PATENT DOCUMENTS

| | | |
|---|---|---|
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0257324 A1 | 9/2014 | Fain |

(56) References Cited

U.S. PATENT DOCUMENTS

| | | |
|---|---|---|
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0121127 A1 | 5/2016 | Klimovitch et al. |
| 2016/0121128 A1 | 5/2016 | Fishler et al. |
| 2016/0121129 A1 | 5/2016 | Persson et al. |

FOREIGN PATENT DOCUMENTS

| | | |
|---|---|---|
| AU | 2014203793 A1 | 7/2014 |
| CA | 1003904 A1 | 1/1977 |
| CN | 202933393 | 5/2013 |
| EP | 0253505 A2 | 1/1988 |
| EP | 0308536 A1 | 3/1989 |
| EP | 0360412 A1 | 3/1990 |
| EP | 0362611 | 4/1990 |
| EP | 0401962 A2 | 12/1990 |
| EP | 0469817 A2 | 2/1992 |
| EP | 503823 A2 | 9/1992 |
| EP | 0506230 A1 | 9/1992 |
| EP | 0554208 A2 | 8/1993 |
| EP | 0597459 A2 | 5/1994 |
| EP | 0617980 A2 | 10/1994 |
| EP | 0711531 A1 | 5/1996 |
| EP | 0744190 A2 | 11/1996 |
| EP | 0748638 A2 | 12/1996 |
| EP | 0784996 A1 | 7/1997 |
| EP | 0848965 A2 | 6/1998 |
| EP | 0879621 A2 | 11/1998 |
| EP | 0919256 A1 | 6/1999 |
| EP | 0993842 A1 | 4/2000 |
| EP | 1112756 A2 | 7/2001 |
| EP | 1702648 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 | 2/2013 |
| WO | 9302746 A1 | 2/1993 |
| WO | 9401173 A1 | 1/1994 |
| WO | 9500202 | 1/1995 |
| WO | 9636134 | 11/1996 |
| WO | 9739681 A1 | 10/1997 |
| WO | 9739799 A1 | 10/1997 |
| WO | 9825669 A1 | 6/1998 |
| WO | 9826840 | 6/1998 |
| WO | 9840010 A1 | 9/1998 |
| WO | 9848891 A1 | 11/1998 |
| WO | 9853879 A1 | 12/1998 |
| WO | 9915232 A1 | 4/1999 |
| WO | 9939767 | 8/1999 |
| WO | 0053089 A1 | 9/2000 |
| WO | 0059573 A1 | 10/2000 |
| WO | 0113993 A1 | 3/2001 |
| WO | 0126733 A1 | 4/2001 |
| WO | 0234330 | 1/2003 |
| WO | 02098282 | 5/2003 |
| WO | 03047690 A2 | 6/2003 |
| WO | 2005000206 A3 | 4/2005 |
| WO | 2005042089 A1 | 5/2005 |
| WO | 2005089643 A1 | 9/2005 |
| WO | 2006020198 A2 | 2/2006 |
| WO | 2006020198 A3 | 5/2006 |
| WO | 2006049767 A1 | 5/2006 |
| WO | 2006086435 A3 | 8/2006 |
| WO | 2006113659 A1 | 10/2006 |
| WO | 2006124833 A2 | 11/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |

OTHER PUBLICATIONS

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration, Jan. 29, 2016, 15 pages.

Spickler et al., "Totally Self-Contained Intracardiac Pacemaker," Journal of Electrocardiology, vol. 3(3&4): 324-331, 1970.

"Instructions for Use System 1, Leadless Cardiac Pacemaker (LCP) and Delivery Catheter," Nanostim Leadless Pacemakers, pp. 1-28, 2013.

(56) References Cited

OTHER PUBLICATIONS

Juru et al., "The Potential for Inappropriate Ventricular Tachycardia Confirmation Using the Intracardiac Electrogram :EGM) Width Criterion", Pacing and Clinical Electrophysiology [PACE], 22(7): 1039-1046, Jul. 1999.

Hughes et al., "The Effects of Electrode Position on the Detection of the Transvenous Cardiac Electrogram", PACE, 3(6): 651-655, Nov. 1980.

International Search Report and Written Opinion for Application No. PCT/US2005/035057, 17 pages, date mailed Feb. 1, 2006.

Kinoshita et al., "Letter to the Editor", Journal of Electrocardiology, 29(3): 255-256, Jul. 1996.

Leitch et al., "Feasibility of an Implantable Arrhythmia Monitor", PACE, 15(12): 2232-2235, Dec. 1992.

Mazur et al., "Functional Similarity Between Electrograms Recorded from an Implantable Cardioverter Defibrillator Emulator and the Surface Electrocardiogram", PACE, 24(1): 34-40, Jan. 2001.

Medtronic, "Marquis™ DR 7274 Dual Chamber Implantable Cardioverter Defibrillator", Reference Manual, 426 pgs., Feb. 2002.

Morris et al., "Detection of Atrial Arrhythmia for Cardiac Rhythm Management by Implantable Devices", Journal of Electrocardiology, vol. 33, Supplement 1, pp. 133-139, 2000.

Theres et al., "Electrogram Signals Recorded from Acute and Chronic Pacemaker Implantation Sites in Pacemaker Patients", PACE, 21(1): 11-17, Jan. 1998.

SYSTEMS AND METHODS FOR DETECTING CARDIAC ARRHYTHMIAS

CROSS-REFERENCES TO RELATED APPLICATIONS

This application claims the benefit of U.S. Provisional Application No. 61/926,051, filed Jan. 10, 2014, the complete disclosure of which is herein incorporated by reference.

TECHNICAL FIELD

The present disclosure generally relates to systems, devices, and methods for detecting cardiac arrhythmias, and more specifically to multiple device systems, methods, and devices for detecting and identifying cardiac arrhythmias.

BACKGROUND

Pacing instruments can be used to treat patients suffering from various heart conditions that may result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, a patient may have multiple implanted devices.

SUMMARY

The present disclosure relates generally to systems and methods for coordinating detection and/or treatment of abnormal heart activity using multiple implanted devices within a patient. It is contemplated that the multiple implanted devices may include, for example, pacemakers, defibrillators, diagnostic devices, and/or any other suitable implantable devices, as desired.

In one example, a leadless cardiac pacemaker (LCP) may be implanted to aid in determining and/or treating a tachyarrhythmia. Cardiac activity of the heart can be sensed using one or more leadless cardiac pacemakers (LCPs) either alone or in combination with one or more other devices. The leadless cardiac pacemakers (LCPs) can be implanted in close proximity to the heart, such as in or on the heart. In some instances, sensing cardiac activity by the one or more leadless cardiac pacemakers (LCPs) can help the system determine an occurrence of cardiac arrhythmia. For treatment purposes, electrical stimulation therapy, for example anti-tachyarrhythmia pacing (ATP) therapy, may be delivered by at least one of the implanted devices. Such therapy can help treat the detected cardiac arrhythmia.

An illustrative method of identifying a tachyarrhythmia of a heart may include: sensing cardiac activity by a medical device, sensing cardiac activity by a first leadless cardiac pacemaker, wherein the first leadless cardiac pacemaker is spaced from the medical device and communicatively coupled to the medical device via a communication pathway that includes the body of the patient, and determining if a tachyarrhythmia is occurring based, at least in part, on both the cardiac activity sensed by the medical device and the cardiac activity sensed by the first leadless cardiac pacemaker.

Another illustrative method of identifying a tachyarrhythmia of a heart of a patient may include: sensing cardiac activity by a medical device; sensing cardiac activity by a first leadless cardiac pacemaker, wherein the first leadless cardiac pacemaker is communicatively coupled to the medical device via a communication pathway that includes the body of the patient; determining, by one or more of the medical device and the first leadless cardiac pacemaker, if a tachyarrhythmia is occurring based, at least in part, on the cardiac activity sensed by the medical device and/or the cardiac activity sensed by the first leadless cardiac pacemaker; and after determining a tachyarrhythmia is occurring, determining, by one or more of the medical device and the first leadless cardiac pacemaker, a type of the tachyarrhythmia based, at least in part, on both the cardiac activity sensed by the medical device and the cardiac activity sensed by the first leadless cardiac pacemaker.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
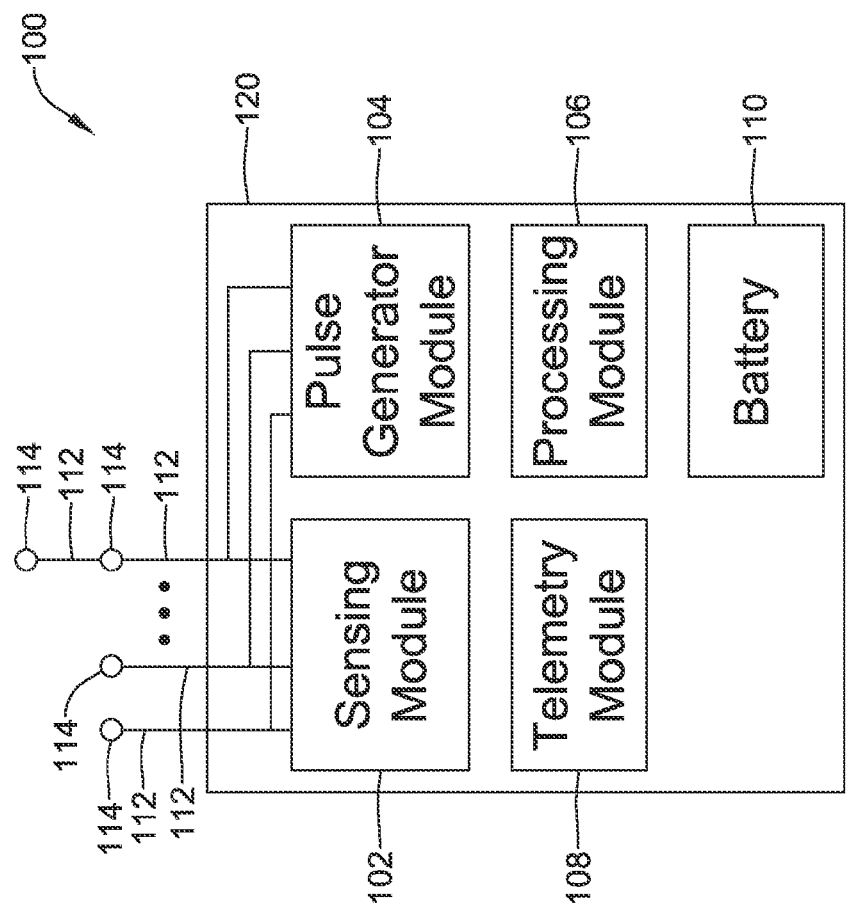
FIG. 1 illustrates a block diagram of an exemplary medical device that may be used in accordance with various examples of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate. In some cases such an abnormality can develop into a fibrillation state, where the contraction of the patient's heart is almost completely desynchronized and the heart pumps very little to no blood.

Many medical device systems have been developed to assist patients who experience such abnormalities. For example, systems have been developed to sense intrinsic cardiac electrical signals and, based on the sensed electrical signals, determine whether the patient is suffering from one or more arrhythmias. Such systems may also include the ability to deliver electrical stimulation to the heart of the patient in order to treat the detected arrhythmias. In one example, some medical device systems include the ability to identify when the heart is beating at too low of a rate, termed bradycardia. Such systems may deliver electrical stimulation therapy, or "pacing" pulses, that cause the heart to contract at a higher, safer rate. Some medical device systems are able to determine when a heart is beating at too fast of a rate, termed tachycardia. Such systems may further include one or more anti-tachycardia pacing (ATP) therapies. One such ATP therapy includes delivering electrical stimulation pulses to the heart at a rate faster than the intrinsically generated signals. Although this may temporarily cause the heart to beat faster, such a stimulation protocol may cause the heart to contract in response to the delivered pacing pulses as opposed to the intrinsically generated signals. The ATP therapy may then slow down the rate of the delivered pacing pulses, thereby reducing the heart rate to a lower, safer level.

Other medical device systems may be able to detect fibrillation states and asynchronous contractions. For example, based on the sensed signals, some systems may be able to determine when the heart is in a fibrillation state. Such systems may further be configured to treat such fibrillation states with electrical stimulation therapy. One such therapy includes deliver of a relatively large amount of electrical energy to the heart (a "defibrillation pulse") with the goal of overpowering any intrinsically generated signals. Such a therapy may "reset" the heart, from an electrical standpoint, which may allow for normal electrical processes to take over. Other medical systems may be able to sense that intrinsically generated signals are generated at differing times or that the heart conducts such signals at differing rates. These abnormalities may result in an unsynchronized, inefficient cardiac contraction. The system may further include the ability to administer one or more cardiac resynchronization therapies (CRTs). One such CRT may include delivering electrical stimulation to the heart at differing locations on and/or within the heart. Such methods may help the disparate parts of the heart to contract near simultaneously, or in a synchronized manner if the system delivers the electrical stimulation to the disparate locations at differing times.

The present disclosure relates generally to systems and methods for coordinating detection and/or treatment of abnormal heart activity using multiple implanted devices within a patient. In some instances, a medical device system may include a plurality of devices for detecting cardiac arrhythmias and delivering electrical stimulation therapy. For example, illustrative systems may include devices such as subcutaneous cardioverter-defibrillators (S-ICD), external cardioverter-defibrillators, implantable cardiac pacemakers (ICP), leadless cardiac pacemakers (LCPs), and/or diagnostic only devices (devices that may sense cardiac electrical signals and/or determine arrhythmias but do not deliver electrical stimulation therapies).

FIG. 1 illustrates a block diagram of an exemplary medical device 100 (referred to hereinafter as, MD 100) that may be used in accordance with various examples of the present disclosure. In some cases, the MD 100 may be used for sensing intrinsic cardiac activity, determining occurrences of arrhythmias, and delivering electrical stimulation in response to determining an occurrence of an arrhythmia. In some instances, MD 100 can be implanted within a patient's body, at a particular location (e.g., in close proximity to the patient's heart), to sense and/or regulate the cardiac activity of the heart. In other examples, MD 100 may be located externally to a patient to sense and/or regulate the cardiac activity of the heart. In one example, cardiac contractions generally result from electrical signals that are intrinsically generated by a heart. These electrical signals conduct through the heart tissue, causing the muscle cells of the heart to contract. MD 100 may include features that allow MD 100 to sense such electrical signals and/or other physical parameters (e.g. mechanical contraction, heart sounds, blood pressure, blood-oxygen levels, etc.) of the heart. Such electrical signals and/or physical properties may be considered "cardiac activity." MD 100 may include the ability to determine occurrences of arrhythmias based on the sensed cardiac activity. In some examples, MD 100 may be able to deliver electrical stimulation to the heart in order to treat any detected arrhythmias. For example, MD 100 may be configured to deliver electrical stimulation, pacing pulses, defibrillation pulses, and/or the like in order to implement one or more therapies, such as bradycardia therapy, ATP therapy, CRT, defibrillation, or other electrical stimulation therapies.

FIG. 1 is an illustration of one example medical device 100. The illustrative MD 100 may include a sensing module 102, a pulse generator module 104, a processing module 106, a telemetry module 108, and a battery 110, all housed within a housing 120. MD 100 may further include leads 112, and electrodes 114 attached to housing 120 and in electrical communication with one or more of the modules 102, 104, 106, and 108 housed within housing 120.

Leads 112 may be connected to and extend away from housing 120 of MD 100. In some examples, leads 112 are implanted on or within the heart of the patient, such as heart 115. Leads 112 may contain one or more electrodes 114 positioned at various locations on leads 112 and distances from housing 120. Some leads 112 may only include a single electrode 114 while other leads 112 may include multiple electrodes 114. Generally, electrodes 114 are positioned on leads 112 such that when leads 112 are implanted within the patient, one or more electrodes 114 are in contact with the patient's cardiac tissue. Accordingly, electrodes 114 may conduct intrinsically generated electrical signals to leads 112. Leads 112 may, in turn, conduct the received electrical signals to one or more modules 102, 104, 106, and 108 of MD 100. In a similar manner, MD 100 may generate electrical stimulation, and leads 112 may conduct the generated electrical stimulation to electrodes 114. Electrodes 114 may then conduct the electrical signals to the cardiac tissue of the patient. When discussing sensing intrinsic signals and delivering electrical stimulation, this disclosure may consider such conduction implicit in those processes.

Sensing module 102 may be configured to sense the cardiac electrical activity of the heart. For example, sensing module 102 may be connected to leads 112 and electrodes 114 through leads 112 and sensing module 102 may be configured to receive cardiac electrical signals conducted through electrodes 114 and leads 112. In some examples, leads 112 may include various sensors, such as accelerometers, blood pressure sensors, heart sound sensors, blood-oxygen sensors, and other sensors which measure physiological parameters of the heart and/or patient. In other examples, such sensors may be connected directly to sensing module 102 rather than to leads 112. In any case, sensing module 102 may be configured to receive such signals produced by any sensors connected to sensing module 102, either directly or through leads 112. Sensing modules 102 may additionally be connected to processing module 106 and may be configured to communicate such received signals to processing module 106.

Pulse generator module 104 may be connected to electrodes 114. In some examples, pulse generator module 104 may be configured to generate an electrical stimulation signals to provide electrical stimulation therapy to the heart. For example, pulse generator module 104 may generate such a signal by using energy stored in battery 110 within MD 100. Pulse generator module 104 may be configured to generate electrical stimulation signals in order to provide one or multiple of a number of different therapies. For example, pulse generator module 104 may be configured to generate electrical stimulation signals to provide bradycardia therapy, tachycardia therapy, cardiac resynchronization therapy, and fibrillation therapy. Bradycardia therapy may include generating and delivering pacing pulses at a rate faster than the intrinsically generated electrical signals in order to try to increase the heart rate. Tachycardia therapy may include ATP therapy as described herein. Cardiac resynchronization therapy may include CRT therapy also described herein. Fibrillation therapy may include delivering a fibrillation pulse to try to override the heart and stop the fibrillation state. In other examples, pulse generator 104 may be configured to generate electrical stimulation signals to provide electrical stimulation therapies different than those described herein to treat one or more detected arrhythmias.

Processing module 106 can be configured to control the operation of MD 100. For example, processing module 106 may be configured to receive electrical signals from sensing module 102. Based on the received signals, processing module 106 may be able to determine occurrences of arrhythmias. Based on any determined arrhythmias, processing module 106 may be configured to control pulse generator module 104 to generate electrical stimulation in accordance with one or more therapies to treat the determined one or more arrhythmias. Processing module 106 may further receive information from telemetry module 108. In some examples, processing module 106 may use such received information in determining whether an arrhythmia is occurring or to take particular action in response to the information. Processing module 106 may additionally control telemetry module 108 to send information to other devices.

In some examples, processing module 106 may include a pre-programmed chip, such as a very-large-scale integration (VLSI) chip or an application specific integrated circuit (ASIC). In such embodiments, the chip may be pre-programmed with control logic in order to control the operation of MD 100. By using a pre-programmed chip, processing module 106 may use less power than other programmable circuits while able to maintain basic functionality, thereby increasing the battery life of MD 100. In other examples, processing module 106 may include a programmable microprocessor. Such a programmable microprocessor may allow a user to adjust the control logic of MD 100, thereby allowing for greater flexibility of MD 100 than when using a pre-programmed chip. In some examples, processing module 106 may further include a memory circuit and processing module 106 may store information on and read information from the memory circuit. In other examples, MD 100 may include a separate memory circuit (not shown) that is in communication with processing module 106, such that processing module 106 may read and write information to and from the separate memory circuit.

Telemetry module 108 may be configured to communicate with devices such as sensors, other medical devices, or the like, that are located externally to MD 100. Such devices may be located either external or internal to the patient's body. Irrespective of the location, external devices (i.e. external to the MD 100 but not necessarily external to the patient's body) can communicate with MD 100 via telemetry module 108 to accomplish one or more desired functions. For example, MD 100 may communicate sensed electrical signals to an external medical device through telemetry module 108. The external medical device may use the communicated electrical signals in determining occurrences of arrhythmias. MD 100 may additionally receive sensed electrical signals from the external medical device through telemetry module 108, and MD 100 may use the received sensed electrical signals in determining occurrences of arrhythmias. Telemetry module 108 may be configured to use one or more methods for communicating with external devices. For example, telemetry module 108 may communicate via radiofrequency (RF) signals, inductive coupling, optical signals, acoustic signals, conducted communication signals, or any other signals suitable for communication. Communication techniques between MD 100 and external devices will be discussed in further detail with reference to FIG. 3 below.

Battery 110 may provide a power source to MD 100 for its operations. In one example, battery 110 may be a non-rechargeable lithium-based battery. In other examples, the non-rechargeable battery may be made from other suitable materials known in the art. Because, in examples where MD 100 is an implantable device, access to MD 100 may be limited, it is necessary to have sufficient capacity of the battery to deliver sufficient therapy over a period of treatment such as days, weeks, months, or years. In other examples, battery 110 may a rechargeable lithium-based battery in order to facilitate increasing the useable lifespan of MD 100.

In general, MD 100 may be similar to one of a number of existing medical devices. For example, MD 100 may be similar to various implantable medical devices. In such examples, housing 120 of MD 100 may be implanted in a transthoracic region of the patient. Housing 120 may generally include any of a number of known materials that are safe for implantation in a human body and may, when implanted, hermetically seal the various components of MD 100 from fluids and tissues of the patient's body.

In some examples, MD 100 may be an implantable cardiac pacemaker (ICP). In such an example, MD 100 may have one or more leads, for example leads 112, which are implanted on or within the patient's heart. The one or more leads 112 may include one or more electrodes 114 that are in contact with cardiac tissue and/or blood of the patient's heart. MD 100 may also be configured to sense intrinsically generated cardiac electrical signals and determine, for example, one or more cardiac arrhythmias based on analysis of the sensed signals. MD 100 may further be configured to deliver CRT, ATP therapy, bradycardia therapy, defibrillation therapy and/or other therapy types via leads 112 implanted within the heart.

In some instances, MD 100 may be a subcutaneous cardioverter-defibrillator (S-ICD). In such examples, one of leads 112 may include a subcutaneously implanted lead. In some cases, MD 100 may be configured to sense intrinsically generated cardiac electrical signals and determine one or more cardiac arrhythmias based on analysis of the sensed signals. MD 100 may further be configured to deliver one or more defibrillation pulses in response to determining an arrhythmia. In other examples, MD 100 may be an implantable cardioverter-defibrillator (ICD), where one or more of leads 112 may be implanted within heart 115.

Figure 2:
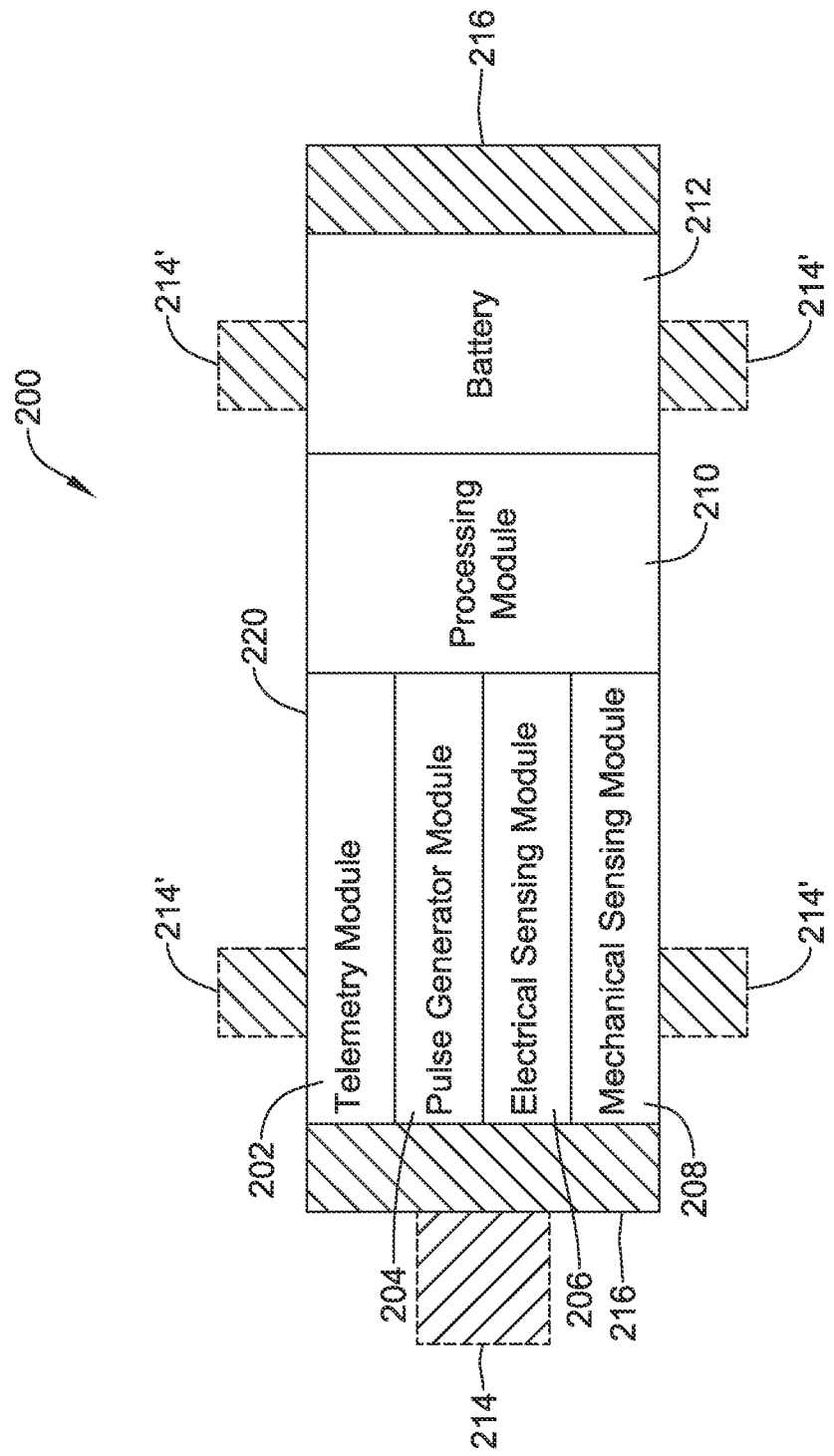
FIG. 2 illustrates an exemplary leadless cardiac pacemaker (LCP) having electrodes, according to one example of the present disclosure.

In still other examples, MD 100 may be a leadless cardiac pacemaker (LCP—described more specifically with respect to FIG. 2). In such examples, MD 100 may not include leads 112 that extend away from housing 120. Rather, MD 100 may include electrodes 114 coupled relative to the housing 120. In these examples, MD 100 may be implanted on or within the patient's heart at a desired location, and may be configured to deliver CRT, ATP therapy, bradycardia therapy, and/or other therapy types via electrodes 114.

In some instances, MD 100 may be a diagnostic-only device. In some cases, MD 100 may be configured to sense, or receive, cardiac electrical signals and/or physical parameters such as mechanical contraction, heart sounds, blood pressure, blood-oxygen levels, etc. MD 100 may further be configured to determine occurrences of arrhythmias based on the sensed or received cardiac electrical signals and/or physical parameters. In one example, MD 100 may do away with pulse generation module 104, as MD 100 may not be configured to deliver electrical stimulation in response to determining an occurrence of an arrhythmia. Rather, in order to respond to detected cardiac arrhythmias, MD 100 may be part of a system of medical devices. In such a system, MD 100 may communicate information to other devices within the system and one or more of the other devices may take action, for example delivering electrical stimulation therapy, in response to the receive information from MD 100. The term pulse generator may be used to describe any such device that is capable of delivering electrical stimulation therapy to the heart, such as an ICD, ICP, LCP, or the like.

In some examples, MD 100 may not be an implantable medical device. Rather, MD 100 may be a device external to the patient's body, and may include skin-electrodes that are placed on a patient's body. In such examples, MD 100 may be able to sense surface cardiac electrical signals (e.g. electrical signals that are generated by the heart or device implanted within a patient's body and conducted through the body to the skin). In such examples, MD 100 may still be configured to deliver various types of electrical stimulation therapy. In other examples, however, MD 100 may be a diagnostic-only device.

FIG. 2 is an illustration of an exemplary leadless cardiac pacemaker (LCP) 200. In the example shown, LCP 200 may include all of the modules and components of MD 100, except that LCP 200 may not include leads 112. As can be seen in FIG. 2, LCP 200 may be a compact device with all components housed within LCP 200 or directly on housing 220. As illustrated in FIG. 2, LCP 200 may include telemetry module 202, pulse generator module 204, processing module 210, and battery 212. Such components may have a similar function to the similarly named modules and components as discussed in conjunction with MD 100 of FIG. 1.

In some examples, LCP 200 may include electrical sensing module 206 and mechanical sensing module 208. Electrical sensing module 206 may be similar to sensing module 102 of MD 100. For example, electrical sensing module 206 may be configured to receive electrical signals generated intrinsically by the heart. Electrical sensing module 206 may be in electrical connection with electrodes 214, which may conduct the intrinsically generated electrical signals to electrical sensing module 206. Mechanical sensing module 208 may be configured to receive one or more signals representative of one or more physiological parameters of the heart. For example, mechanical sensing module 208 may include, or be in electrical communication with one or more sensors, such as accelerometers, blood pressure sensors, heart sound sensors, blood-oxygen sensors, and other sensors which measure physiological parameters of the patient. Although described with respect to FIG. 2 as separate sensing modules, in some examples, electrical sensing module 206 and mechanical sensing module 208 may be combined into a single module.

In at least one example, each of modules 202, 204, 206, 208, and 210 illustrated in FIG. 2 may be implemented on a single integrated circuit chip. In other examples, the illustrated components may be implemented in multiple integrated circuit chips that are in electrical communication with one another. All of modules 202, 204, 206, 208, and 210 and battery 212 may be encompassed within housing 220. Housing 220 may generally include any material that is known as safe for implantation within a human body and may hermetically seal modules 202, 204, 206, 208, and 210 and battery 212 from fluids and tissues when LCP 200 is implanted within a patient.

As depicted in FIG. 2, LCP 200 may include electrodes 214, which can be secured relative to housing 220 but exposed to the tissue and/or blood surrounding the LCP 200. As such, electrodes 214 may be generally disposed on either end of LCP 200 and may be in electrical communication with one or more of modules 202, 204, 206, 208, and 210. In some examples, electrodes 214 may be connected to housing 220 only through short connecting wires such that electrodes 214 are not directly secured relative to housing 220. In some examples, LCP 200 may additionally include one or more electrodes 214'. Electrodes 214' may be positioned on the sides of LCP 200 and increase the number of electrodes by which LCP 200 may sense cardiac electrical activity and/or deliver electrical stimulation. Electrodes 214 and/or 214' can be made up of one or more biocompatible conductive materials such as various metals or alloys that are known to be safe for implantation within a human body. In some instances, electrodes 214 and/or 214' connected to LCP 200 may have an insulative portion that electrically isolates the electrodes 214 from, adjacent electrodes, the housing 220, and/or other materials.

To implant LCP 200 inside patient's body, an operator (e.g., a physician, clinician, etc.), may need to fix LCP 200 to the cardiac tissue of the patient's heart. To facilitate fixation, LCP 200 may include one or more anchors 216. Anchor 216 may be any one of a number of fixation or anchoring mechanisms. For example, anchor 216 may include one or more pins, staples, threads, screws, helix, tines, and/or the like. In some examples, although not shown, anchor 216 may include threads on its external surface that may run along at least a partial length of anchor 216. The threads may provide friction between the cardiac tissue and the anchor to help fix anchor 216 within the cardiac tissue. In other examples, anchor 216 may include other structures such as barbs, spikes, or the like to facilitate engagement with the surrounding cardiac tissue.

The design and dimensions of MD 100 and LCP 200, as shown in FIGS. 1 and 2, respectively, can be selected based on various factors. For example, if the medical device is for implant on the endocardial tissue, such as is sometimes the case of an LCP, the medical device can be introduced through a femoral vein into the heart. In such instances, the dimensions of the medical device may be such as to be navigated smoothly through the tortuous path of the vein without causing any damage to surrounding tissue of the vein. According to one example, the average diameter of the femoral vein may be between about 4 mm to about 8 mm in width. For navigation to the heart through the femoral vein, the medical device can have a diameter of at less than 8 mm. In some examples, the medical device can have a cylindrical shape having a circular cross-section. However, it should be noted that the medical device can be made of any other suitable shape such as rectangular, oval, etc. A flat, rectangular-shaped medical device with a low profile may be desired when the medical device is designed to be implanted subcutaneously.

FIGS. 1 and 2 above described various examples of MD 100. In some examples, a medical device system may include more than one medical device. For example, multiple medical devices 100/200 may be used cooperatively to detect and treat cardiac arrhythmias and/or other cardiac abnormalities. Some example systems will be described below in connection with FIGS. 3-10. In such multiple device systems, it may be desirable to have a medical device communicate with another medical device, or at least receive various communication signals from another medical device.

Figure 3:
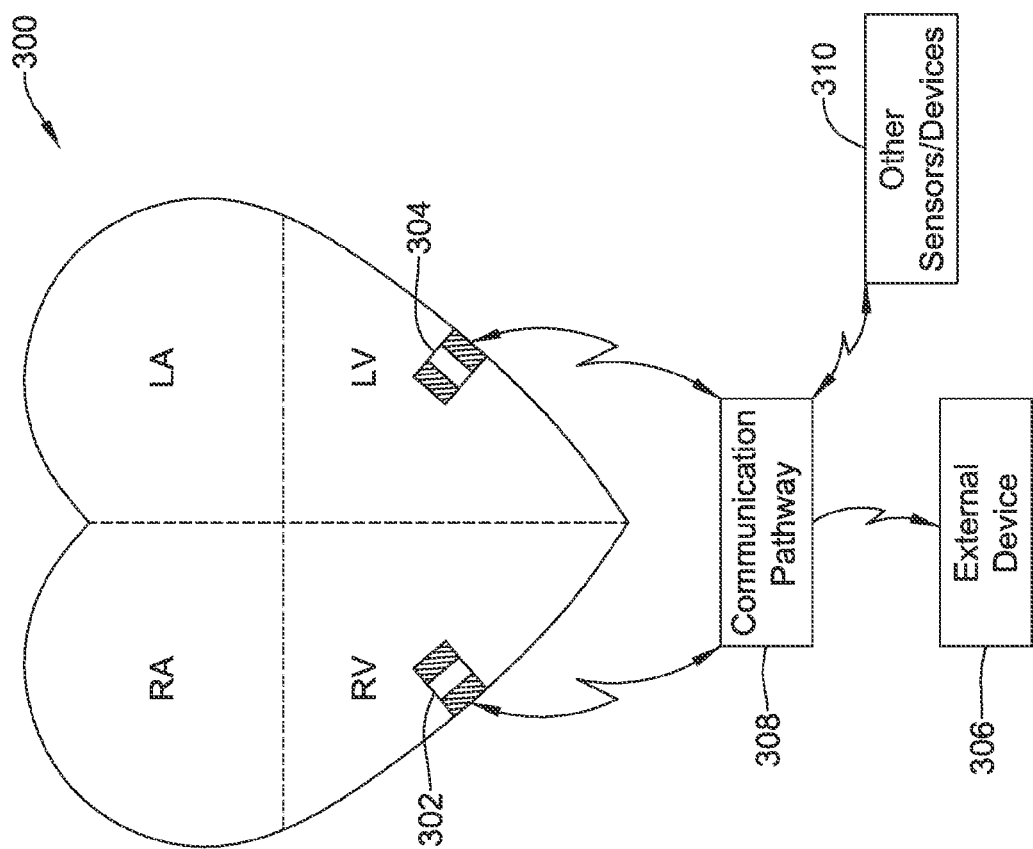
FIG. 3 is a schematic diagram of an exemplary medical system that includes multiple leadless cardiac pacemakers (LCPs) and/or other devices in communication with one another of the present disclosure.

FIG. 3 illustrates an example of a medical device system and a communication pathway via which multiple medical devices may communicate. In the example shown, medical device system 300 may include LCPs 302 and 304, external medical device 306, and other sensors/devices 310. External device 306 may be any of the devices described previously with respect to MD 100. Other sensors/devices 310 may also be any of the devices described previously with respect to MD 100. In other examples, other sensors/devices 310 may include a sensor, such as an accelerometer or blood pressure sensor, or the like. In still other examples, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one example, external device 306 may receive such signals and, based on the received signals, determine an occurrence of an arrhythmia. In some cases, external device 306 may communicate such determinations to one or more other devices 302/304, 306, and 310 of system 300. Additionally, one or more other devices 302/304, 306, and 310 of system 300 may take action based on the communicated determination of an arrhythmia, such as by delivering a suitable electrical stimulation. This description is just one of many reasons for communication between the various devices of system 300.

Communication pathway 308 may represent one or more of various communication methods. For example, the devices of system 300 may communicate with each other via RF signals, inductive coupling, optical signals, acoustic signals, or any other signals suitable for communication and communication pathway 308 may represent such signals.

In at least one example, communicated pathway 308 may represent conducted communication signals. Accordingly, devices of system 300 may have components that allow for conducted communication. In examples where communication pathway 308 includes conducted communication signals, devices of system 300 may communicate with each other by sensing electrical communication pulses delivered into the patient's body by another device. The patient's body may conduct these electrical communication pulses to the other devices of system 300. In such examples, the delivered electrical communication pulses may differ from the electrical stimulation pulses of any of the above described electrical stimulation therapies. For example, the devices of system 300 may deliver such electrical communication pulses at a voltage level that is sub-threshold. That is, the voltage amplitude of the delivered electrical communication pulses may be low enough as to not capture the heart (e.g. not cause a contraction). Although, in some circumstances, one or more delivered electrical communication pulses may capture the heart, and in other circumstances, delivered electrical stimulation pulses may not capture the heart. In some cases, the delivered electrical communication pulses may be modulated (e.g. pulse width modulated), or the timing of the delivery of the communication pulses may be modulates, to encode the communicated information. These are just some examples.

As mentioned above, some example systems may employ multiple devices for determining occurrences of arrhythmias, and/or for delivering electrical stimulation therapy in response to determining one or more arrhythmias. FIGS. 3-10 describe various example systems that may use multiple devices in order to determine occurrences of arrhythmias and/or deliver electrical stimulation therapy. However, FIGS. 3-10 should not be viewed as limiting examples. For example, FIGS. 3-10 describe how various multiple device systems may coordinate to detect various arrhythmias. However, any combinations of devices such as that described with respect to MD 100 and LCP 200 may used in concert with the below described techniques for detecting arrhythmias. Additionally, although the below description focuses on how devices of various systems may operate to detect arrhythmias, such devices may additionally operate to deliver electrical stimulation therapy in accordance with one or more techniques, such as described in the co-pending and co-owned provisional applications titled "SYSTEMS AND METHODS FOR TREATING CARDIAC ARRHYTHMIAS", filed on Jan. 10, 2014, and "COMMUNICATION OF THERAPY ACTIVITY OF A FIRST IMPLANTABLE MEDICAL DEVICE TO ANOTHER IMPLANTABLE MEDICAL DEVICE", filed on Jan. 10, 2014, both of which are hereby incorporated by reference in their entirety.

Figure 4:
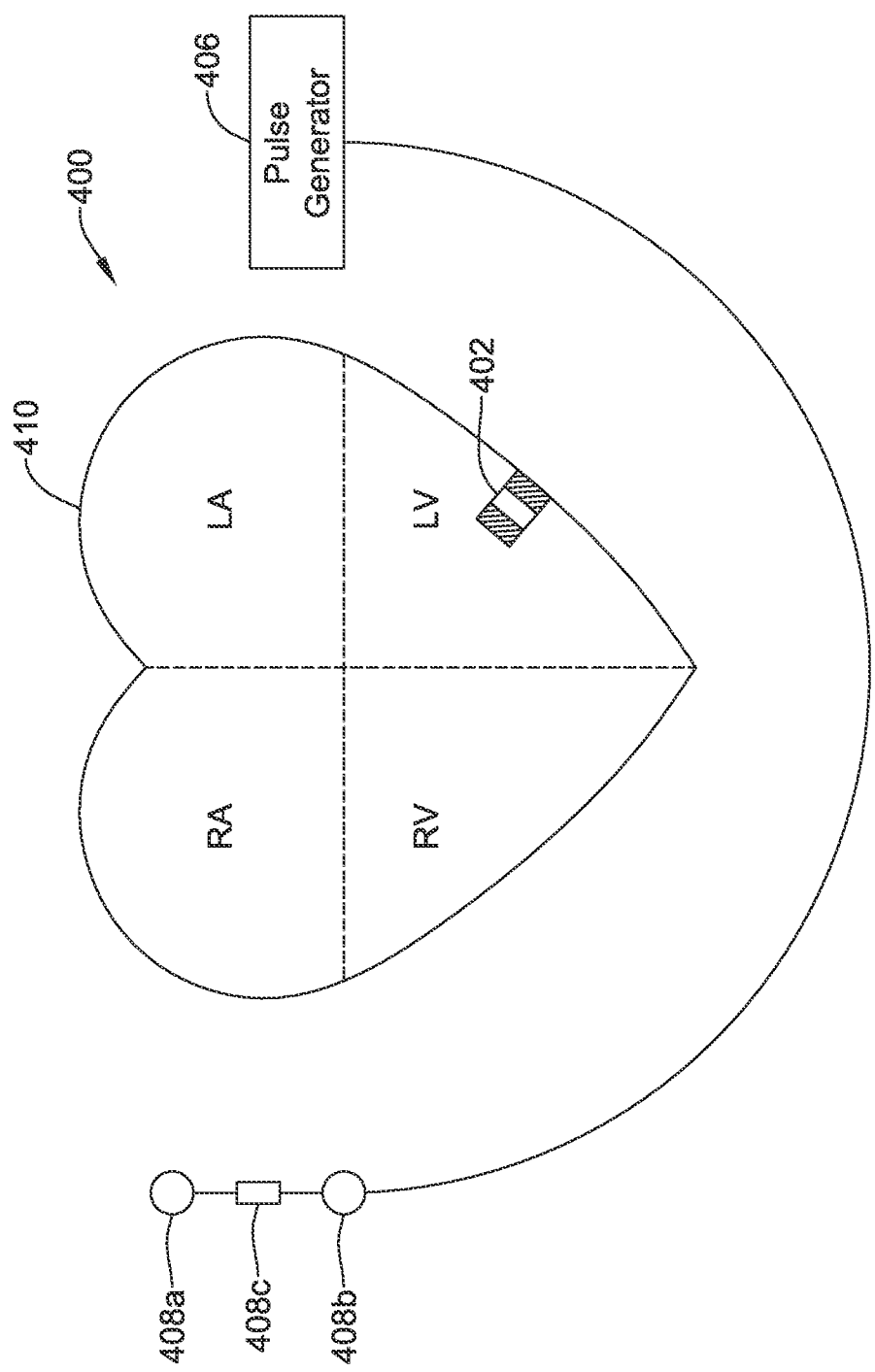
FIG. 4 is a schematic diagram of a system including an LCP and another medical device, in accordance with yet another example of the present disclosure.

FIG. 4 illustrates an example medical device system 400 that includes an LCP 402 and a pulse generator 406. In some examples, pulse generator 406 may be either an external cardioverter-defibrillator or an ICD. For example, pulse generator 406 may be such devices as described previously with respect to MD 100. In some examples, pulse generator 406 may be an S-ICD. In examples where pulse generator 406 is an external cardioverter-defibrillator, electrodes 408a, 408b, and 408c may be skin electrodes that reside on the patient's body. In examples where pulse generator 406 is an S-ICD, electrodes 408a, 408b, and 408c may be attached to a subcutaneous lead that is implanted within the patient's body proximate, but not on or within the heart 410.

As shown, LCP 402 may be implanted within heart 410. Although LCP 402 is depicted as being implanted within the left ventricle (LV) of heart 410, in other examples, LCP 402 may be implanted within a different chamber of the heart 410. For example, LCP 402 may be implanted within the left atrium (LA) of heart 410 or the right atrium (RA) of heart 410. In other examples, LCP 402 may be implanted within the right ventricle (RV) of heart 410.

In any event, LCP 402 and pulse generator 406 may operate together to determine occurrences of cardiac arrhythmias of heart 410. In some instances, devices 402 and 406 may operate independently to sense cardiac activity of heart 410. As described above, cardiac activity may include sensed cardiac electrical signals and/or sensed physiological parameters. In such examples, each of LCP 402 and pulse generator 406 may operate to determine occurrences of arrhythmias independently of one another based on the independently sensed cardiac activity. When a first of LCP 402 or pulse generator 406 makes a first determination of an arrhythmia, that first device may communicate the first determination to the second device. If the second device of system 400 also makes a determination of an arrhythmia, e.g. a second determination of an arrhythmia, based on its own sensed cardiac activity, the arrhythmia may be confirmed and the system 400 may begin to deliver appropriate electrical stimulation therapy to heart 410. In this manner, both devices 402 and 406 of system 400 may be used to determine an occurrence of an arrhythmia. In some examples, when only one of devices 402 or 406 determines an occurrence of an arrhythmia, and the other does not, system 400 may still begin to deliver appropriate electrical stimulation therapy to heart 410.

In other examples, only one of devices 402 and 406 actively senses cardiac activity and determines occurrences of arrhythmias. For example, when the actively sensing device (e.g. LCP 402) determines an occurrence of an arrhythmia, the actively sensing device may communicate the determination to the other device (e.g. Pulse Generator 406) of system 400. System 400 may then begin to deliver appropriate electrical stimulation therapy to heart 410. In another example, the device which actively senses cardiac activity may communicate the sensed cardiac activity to the other device. Then, based on the received cardiac activity, the other device may determine an occurrence of an arrhythmia. System 400 may then begin to deliver appropriate electrical stimulation therapy to heart 410. In some of these examples, the other device may additionally communicate the determination of an arrhythmia to the actively sensing device.

In still other examples, only a first of devices 402 or 406 continuously senses cardiac actively. The first device (e.g. Pulse Generator 406) may continually determine, based on the sensed cardiac activity, occurrences of arrhythmias. In such examples, when the first device determines an occurrence of an arrhythmia, the first device may communicate the determination to the second device (e.g. LCP 402). Upon receiving a determination of an occurrence of an arrhythmia, the second device may begin to sense cardiac activity. Based on its sensed cardiac activity, the second device may also determine an occurrence of an arrhythmia. In such examples, only after the second device also determines an occurrence of an arrhythmia, system 400 may begin to deliver appropriate electrical stimulation therapy to heart 410.

In some examples, determining an occurrence of an arrhythmia may include determining a beginning of an arrhythmia, and system 400 may be configured to determine when to begin to deliver electrical stimulation therapy. In some examples, determining an occurrence of an arrhythmia may include determining an end of an arrhythmia. In such examples, system 400 may be configured to also determine when to cease to deliver electrical stimulation therapy.

In examples where system 400 operates to deliver appropriate electrical stimulation therapy to heart 410, if the determined arrhythmia is a fibrillation, pulse generator 406 may operate to deliver a defibrillation pulse to heart 410. In examples where the determined arrhythmia is a tachycardia, LCP 402 may deliver ATP therapy to heart 410. In examples where the determined arrhythmia is a bradycardia, LCP 402 may deliver bradycardia therapy to heart 410. In examples where the determined arrhythmia is un-synchronized contractions, LCP 402 may deliver CRT to heart 410.

Figure 5:
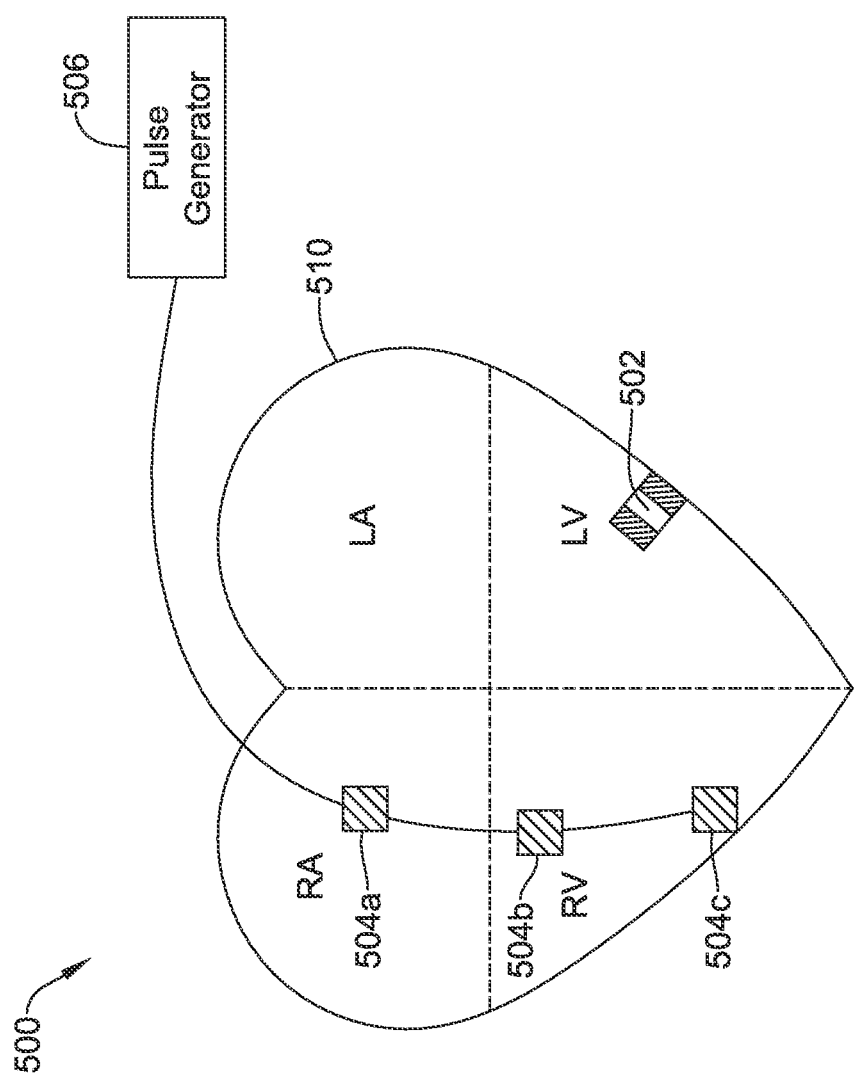
FIG. 5 is a schematic diagram of the a system including an LCP and another medical device, in accordance with another example of the present disclosure.

FIG. 5 illustrates an example medical device system 500 that includes an LCP 502 and a pulse generator 506. In this example, pulse generator 506 may be an implantable cardiac pacemaker (ICP). For example, pulse generator 506 may be an ICP such as that described previously with respect to MD 100. In examples where pulse generator 506 is an ICP, electrodes 504a, 504b, and 504c may be implanted on or within the right ventricle and/or right atrium of heart 510 via one or more leads.

LCP 502 may be implanted within heart 510. Although LCP 502 is depicted implanted within the left ventricle (LV) of the heart 510, in some instances, LCP 502 may be implanted within a different chamber of the heart 510. For example, LCP 502 may be implanted within the left atrium (LA) of heart 510 or the right atrium (RA) of heart 510. In other examples, LCP 502 may be implanted within the right ventricle (RV) of heart 510.

In any event, LCP 502 and pulse generator 506 may operate together to determine occurrences of cardiac arrhythmias of heart 510. In some instances, devices 502 and 506 may operate independently to sense cardiac activity of heart 510. As described above, cardiac activity may include sensed cardiac electrical signals and/or sensed physiological parameters. In some cases, each of LCP 502 and pulse generator 506 may operate to determine occurrences of arrhythmias independently based on the independently sensed cardiac activity. When a first of LCP 502 or pulse generator 506 makes a first determination of an arrhythmia, that first device may communicate the first determination to the second device. If the second device of system 500 also makes a determination of an arrhythmia, e.g. a second determination of an arrhythmia, based on its own sensed cardiac activity, system 500 may confirm the arrhythmia and may begin to deliver appropriate electrical stimulation therapy to heart 510. In this manner, both devices 502 and 506 of system 500 may be used to determine an occurrence of an arrhythmia. In some instances, when only a single one of devices 502 or 506 determines an occurrence of an arrhythmia, system 500 may also begin to deliver appropriate electrical stimulation therapy to heart 510.

In some examples, only one of devices 502 and 506 may actively sense cardiac activity and determine occurrences of arrhythmias. For example, when the actively sensing device (e.g. pulse generator 506) determines an occurrence of an arrhythmia, the actively sensing device may communicate the determination to the other device (e.g. LCP 502) of system 500. System 500 may then begin to deliver appropriate electrical stimulation therapy to heart 510. In some examples, the device which actively senses cardiac activity may communicate the sensed cardiac activity to the other device. Then, based on the received cardiac activity, the other device may sense for and determine an occurrence of an arrhythmia. System 500 may then begin to deliver appropriate electrical stimulation therapy to heart 510. In some instances, the other device may additionally communicate the determination of an arrhythmia to the actively sensing device.

In still other examples, only a first of devices 502 or 506 may continuously sense cardiac actively. The first device may additionally continually determine, based on the sensed cardiac activity, occurrences of arrhythmias. In some examples, when the first device determines an occurrence of an arrhythmia, the first device may communicate the determination to the second device. Upon receiving a determination of an occurrence of an arrhythmia, the second device may begin to sense cardiac activity. Based on its sensed cardiac activity, the second device may also determine an occurrence of an arrhythmia. In such examples, only after the second device also determines an occurrence of an arrhythmia, system 500 may begin to deliver appropriate electrical stimulation therapy to heart 510.

In some examples, determining an occurrence of an arrhythmia may include determining a beginning of an arrhythmia, and system 500 may be configured to determine when to begin to deliver electrical stimulation therapy. In some examples, determining an occurrence of an arrhythmia may include determining an end of an arrhythmia. In such examples, system 500 may be configured to determine when to cease to deliver electrical stimulation therapy. In examples where system 500 does not begin to deliver appropriate electrical stimulation therapy to heart 510 until multiple devices determine an occurrence of a cardiac arrhythmia, each of the determinations that do not trigger delivery of electrical stimulation therapy may be termed provisional determinations.

In examples where system 500 operates to deliver appropriate electrical stimulation therapy to heart 510, if the determined arrhythmia is a tachycardia, either pulse generator 506, LCP 502, or both may deliver ATP therapy to heart 510. In examples where the determined arrhythmia is a bradycardia, either pulse generator 506, LCP 502, or both may deliver bradycardia therapy to heart 510. In examples where the determined arrhythmia is un-synchronized contractions, either pulse generator 506, LCP 502, or both may deliver CRT to heart 510.

Figure 6:
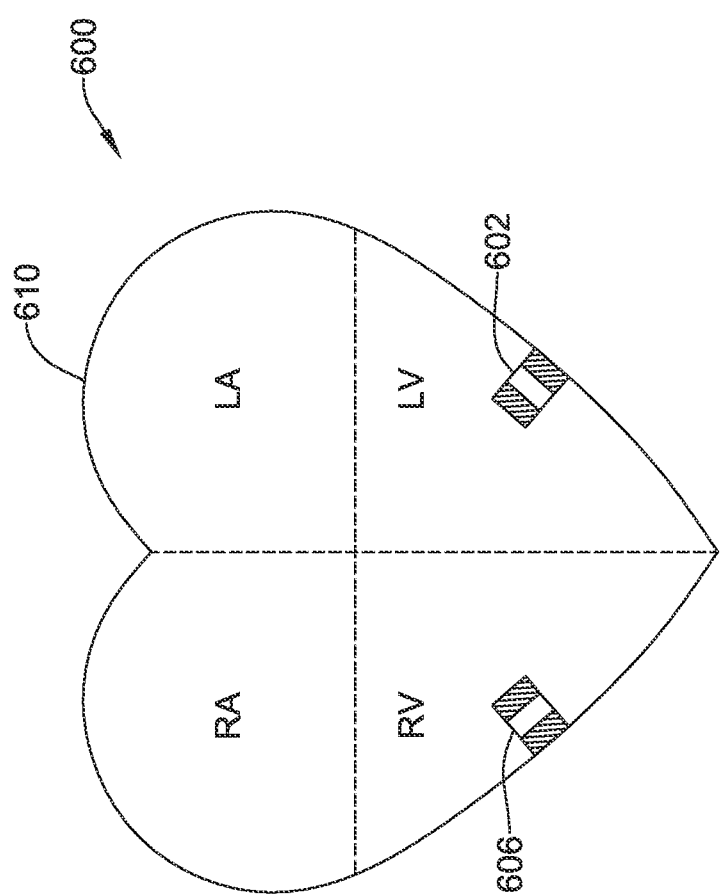
FIG. 6 is a schematic diagram illustrating a multiple leadless cardiac pacemaker (LCP) system in accordance with another example of the present disclosure.

FIG. 6 illustrates an example medical device system 600 that includes LCP 602 and LCP 606. LCP 602 and LCP 606 are shown implanted within heart 610. Although LCPs 602 and 606 are depicted as implanted within the left ventricle (LV) of heart 610 and the right ventricle of heart 610, respectively, in other examples, LCPs 602 and 606 may be implanted within different chambers of heart 610. For example, system 600 may include LCPs 602 and 606 implanted within both atria of heart 610. In other examples, system 600 may include LCPs 602 and 606 implanted within one atrium and one ventricle of heart 610. In more examples, system 600 may include LCPs 602 and 606 implanted within any combination of ventricles and atria. In yet other examples, system 600 may include LCPs 602 and 606 implanted within the same chamber of heart 610.

In any event, and in some examples, LCP 602 and LCP 606 may operate together to determine occurrences of cardiac arrhythmias of heart 610. For example, devices 602 and 606 may operate independently to sense cardiac activity of heart 610. As described above, cardiac activity may include sensed cardiac electrical signals and/or sensed physiological parameters. In such examples, each of LCP 602 and LCP 606 may operate to determine occurrences of arrhythmias independently based on the independently sensed cardiac activity. When a first of LCP 602 or LCP 606 makes a first determination of an arrhythmia, that first device may communicate the first determination to the second device. If the second device of system 600 also makes a determination of an arrhythmia, e.g. a second determination of an arrhythmia, based on its own sensed cardiac activity, system 600 may confirm the arrhythmia and may begin to deliver appropriate electrical stimulation therapy to heart 610. In this manner, both devices 602 and 606 of system 600 may be used to determine an occurrence of an arrhythmia. In some examples, when only a single one of devices 602 or 606 determines an occurrence of an arrhythmia, system 600 may begin to deliver appropriate electrical stimulation therapy to heart 610.

In other examples, only one of devices 602 and 606 may actively sense cardiac activity and determine occurrences of arrhythmias. In some of these examples, when the actively sensing device (e.g. LCP 606) determines an occurrence of an arrhythmia, the actively sensing device may communicate the determination to the other device (e.g. LCP 602) of system 600. System 600 may then begin to deliver appropriate electrical stimulation therapy to heart 610. In some cases, the device which actively senses cardiac activity may communicate the sensed cardiac activity to the other device. Then, based on the received cardiac activity, the other device may determine an occurrence of an arrhythmia. System 600 may then begin to deliver appropriate electrical stimulation therapy to heart 610. In some of these examples, the other device may additionally communicate the determination of an arrhythmia to the actively sensing device and/or to another device.

In some examples, only a first of devices 602 or 606 may continuously sense cardiac actively. The first device may continually determine, based on the sensed cardiac activity, occurrences of arrhythmias. In such examples, when the first device determines an occurrence of an arrhythmia, the first device may communicate the determination to the second device. Upon receiving a determination of an occurrence of an arrhythmia, the second device may begin to sense cardiac activity. Based on its sensed cardiac activity, the second device may also determine an occurrence of an arrhythmia. In such examples, only after the second device also determines an occurrence of an arrhythmia does system 600 begin to deliver appropriate electrical stimulation therapy to heart 610.

In some examples, determining an occurrence of an arrhythmia may include determining a beginning of an arrhythmia, and system 600 may be configured to determine when to begin to deliver electrical stimulation therapy. In some examples, determining an occurrence of an arrhythmia may include determining an end of an arrhythmia. In such examples, system 600 may be configured to also determine when to cease to deliver electrical stimulation therapy. In examples where system 600 does not begin to deliver appropriate electrical stimulation therapy to heart 610 until multiple devices determine an occurrence of a cardiac arrhythmia, each of the determinations that do not trigger delivery of electrical stimulation therapy may be termed provisional determinations.

In examples where system 600 operates to deliver appropriate electrical stimulation therapy to heart 610, if the determined arrhythmia is a tachycardia, either LCP 602, LCP 606, or both may deliver ATP therapy to heart 610. In examples where the determined arrhythmia is a bradycardia, either LCP 602, LCP 606, or both may deliver bradycardia therapy to heart 610. In examples where the determined arrhythmia is un-synchronized contractions, either pulse LCP 602, LCP 606, or both may deliver CRT to heart 610.

Although not necessarily described in FIGS. 4-6, one of the two devices of systems 400, 500, or 600 could be a diagnostic-only device. In such examples, after one or more of the devices determined an occurrence of an arrhythmia, the diagnostic-only device may not deliver any electrical stimulation therapy. Rather, electrical stimulation therapy may be delivered by another device in the system that is capable of delivering appropriate electrical stimulation therapy, if desired.

Figure 7:
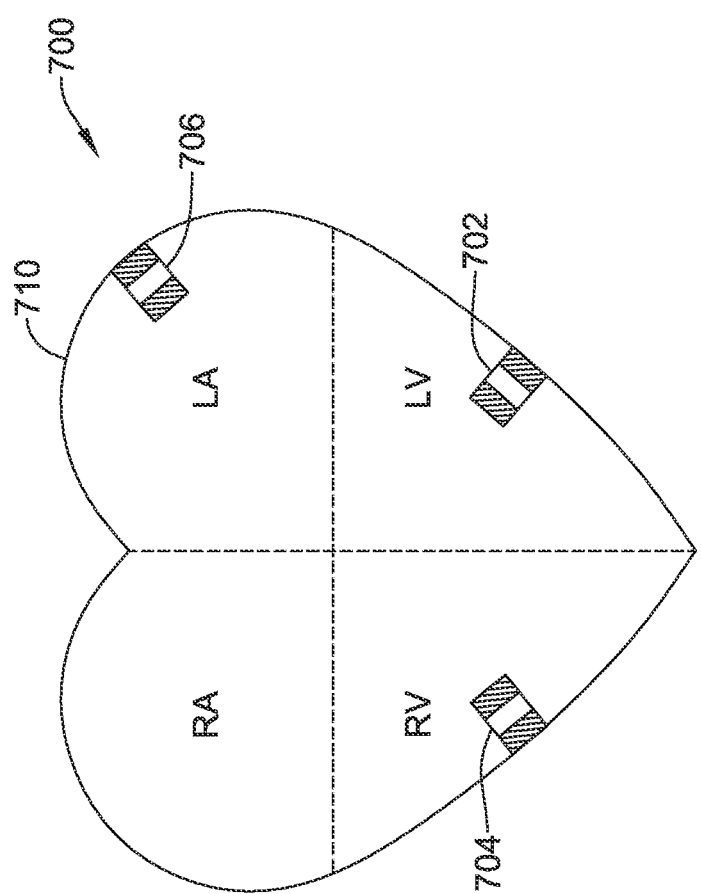
FIG. 7 is a schematic diagram illustrating a multiple leadless cardiac pacemaker (LCP) system, in accordance with yet another example of the present disclosure.

FIG. 7 illustrates an example medical device system 700 with three separate LCPs including LCP 702, LCP 704, and LCP 706. Although system 700 is depicted with LCPs 702, 704, and 706 implanted within the LV, RV, and LA, respectively, other examples may include LCPs 702, 704, and 706 implanted within different chambers of the heart 710. For example, system 700 may include LCPs implanted within both atria and one ventricle of the heart 710. In other examples, system 700 may include LCPs implanted within both ventricles and one atria of heart 710. More generally, it is contemplated that system 700 may include LCPs implanted within any combination of ventricles and atria. In some instances, system 700 may include two or more of LCPs 702, 704, and 706 implanted within the same chamber of the heart 710.

In practice, such a system 700 may operate in accordance with any of the techniques described above with respect to FIGS. 4-6. In some instances, however, system may operate differently, at least to some degree. For example, before system 700 begins to deliver appropriate electrical stimulation therapy to the heart 710, only a majority of LCPs 702, 704, and 706 may need to determine an occurrence of an arrhythmia. For example, in some instances, all of LCPs 702, 704, and 706 may be sensing cardiac activity and determining occurrences of arrhythmias independently. In some cases, only after a majority of LCPs 702, 704, and 706 determined an occurrence of an arrhythmia, may system 700 deliver appropriate electrical stimulation therapy to the heart 710. In some instances, one of the LCP's is designated as the master LCP, and the other slave LCP's may communicate whether they determine an occurrence of an arrhythmia to the master LCP. The master LCP may then determine if a majority of the LCP's 702, 704, and 706 have determined an occurrence of an arrhythmia, and if so, may instruct the delivery of appropriate electrical stimulation therapy to the heart 710. In some instances, the master LCP may instruct particular ones of the LCP's 702, 704, and 706 to deliver electrical stimulation therapy to the heart 710, depending on the type and/or location of the detected arrhythmia.

Alternatively, and in some instances, only a single LCP may need to determine an occurrence of an arrhythmia before system 700 may begin to deliver appropriate electrical stimulation therapy to heart 710. In yet other examples, all three of the LCP's 702, 704, and 706 may need to determine an occurrence of an arrhythmia before system 700 delivers appropriate electrical stimulation therapy to the heart 710.

In some cases, only one LCP 702, 704, and 706 may actively sense cardiac activity and determine an occurrence of an arrhythmia. After determining an occurrence of an arrhythmia, the actively sensing device may communicate the determination to one or both of the other devices. In some cases, one or both of the other devices may then begin sensing for and determining occurrences of arrhythmias. In some instances, when a first one of the other devices determines an occurrence of an arrhythmia, system 700 may begin to deliver appropriate electrical stimulation therapy to heart 710. In other instances, when both of the other devices determine an occurrence of an arrhythmia, system 700 may begin to deliver appropriate electrical stimulation therapy to heart 710.

In some instances, LCPs 702, 704, and 706 may be set up in a daisy-chain configuration. For example, an actively sensing device may send a determination of an arrhythmia to only one of the other two devices (alternatively, only one of the two receiving devices may act upon the received determination from the actively sensing device). The receiving device may then begin actively sensing for and determining occurrences of arrhythmias. Upon determining an occurrence of an arrhythmia, the receiving device may communicate the determination to the last device. The last device may then begin sensing for and determining occurrences of arrhythmias. In some instances, only when the last device determines an occurrence of an arrhythmia does the system 700 begin to deliver appropriate electrical stimulation therapy to heart 710.

Also in accord with the description of systems 400, 500, and 700, in some examples, determining an occurrence of an arrhythmia may include determining a beginning of an arrhythmia, and system 700 may be configured to determine when to begin to deliver electrical stimulation therapy. In some examples, determining an occurrence of an arrhythmia may include determining an end of an arrhythmia. In such examples, system 700 may be configured to determine when to cease delivery of electrical stimulation therapy. In examples where system 700 does not begin to deliver appropriate electrical stimulation therapy to heart 710 until multiple LCP devices determine an occurrence of an arrhythmia, each of the determinations that do not trigger delivery of electrical stimulation therapy may be termed provisional determinations.

In examples where system 700 operates to deliver appropriate electrical stimulation therapy to heart 710, if the determined arrhythmia is a tachycardia, one or more of LCPs 702, 704, and 706 may deliver ATP therapy to heart 710. In examples where the determined arrhythmia is a bradycardia, one or more of LCPs 702, 704, and 706 may deliver bradycardia therapy to heart 710. In examples where the determined arrhythmia is un-synchronized contractions, one or more of LCPs 702, 704, and 706 may deliver CRT to heart 710. It is contemplated that less than all of LCPs 702, 704, and 706 may deliver electrical stimulation therapy in response to the detection of an arrhythmia. For example, only a single of LCPs 702, 704, and 706 may deliver electrical stimulation therapy. In other examples, two of LCPs 702, 704, and 706 may deliver electrical stimulation therapy.

In accordance with the above described description, one can see how such techniques may be extended to systems that have even more than three LCP devices. For example, in a four LCP device system, any of one, two, three, or four devices may be used to determine an occurrence of an arrhythmia before the system begins to deliver appropriate electrical stimulation therapy. In some such examples, all, some, or one of the LCP devices may initially actively sense and determine the occurrences of arrhythmias. In examples where less than all are initially actively sensing, once one of the actively sensing devices determines an occurrence of an arrhythmia, and communicates that determination to other devices of the system, at least one of the other devices of the system may begin to actively sense cardiac activity and determine occurrences of arrhythmias. Again, the techniques described above may be extended to systems that include any number of LCP devices or other devices, such as five, six, seven, or any other number that is practically feasible for implantation within a patient's body.

Additionally, although described above with respect to three or more LCP devices, the same techniques may be applied to any of the systems described with respect to FIGS. 4-5. For example, any of systems 400 and 500 may further include a third device, such as a second LCP device. In such systems, the three devices may operate in accordance with any of the above described techniques of system 700, with the pulse generator capable of sensing for arrhythmias and/or delivering electrical stimulation therapy. In other examples, any of systems 400 and 500 may include a plurality of additional devices. For example, any of systems 400 and 500 may include three, four, five, or any number of LCP devices that are practical for implantation with a patient in addition to pulse generators 406 and 506. Accordingly, in such examples, the devices may operate together in accordance with any of the above described techniques.

A multiple device system may, in some cases, be capable of delivering more effective electrical stimulation therapy than a single device system. For example, before beginning to deliver electrical stimulation therapy, example systems may determine which of the devices of the system first senses a depolarization wave of the heart. In such examples, such systems may direct the device which senses the depolarization wave first to deliver the electrical stimulation therapy. This may allow such systems to deliver electrical stimulation therapy at a site closer to the origin of an arrhythmia, which may increase the effectiveness of the electrical stimulation therapy.

In the example of system 700, one of the devices of system 700 may determine an occurrence of a tachyarrhythmia, either individually or in addition to provisional determinations by other devices of system 700 in accordance with any of the techniques described above. One of the devices of system 700 (e.g. a master device) may determine to deliver ATP therapy to heart 710 or to determine to direct another device of system 700 to deliver ATP therapy. Before either delivering, or directing another device to deliver ATP therapy, one of the devices of system 700 may determine which device of system 700 first senses an intrinsic cardiac depolarization wave of heart 710. The device that senses such a depolarization wave first may then begin delivery of ATP therapy.

The above description is just one example of how a system may operate to deliver electrical stimulation therapy by the device that senses the intrinsic cardiac depolarization wave of a heart first. In other examples, the type of arrhythmia and therapy may be different. Additionally, as such a feature is not tied to any particular configuration or number of devices, any of the systems described herein may further include such a feature. The only limitation in any system may be whether the devices of the system are capable of delivering the appropriate electrical stimulation therapy.

A multiple device system may be used to help provide discrimination between atrial arrhythmias and ventricular arrhythmias. For instance, example systems described herein may operate differently depending on whether an arrhythmia is an atrial arrhythmia or a ventricular arrhythmia in order to more effectively treat such arrhythmias.

As one illustrative example, one of the devices of system 700 may determine an occurrence of a tachyarrhythmia, either individually or in addition to provisional determinations by other devices of system 700 in accordance with any of the techniques described above. Additionally, a device of system 700 may determine whether the tachycardia is an atrial tachycardia or a ventricular tachycardia. If the tachycardia is an atrial tachycardia, one or more of the devices of system 700 may determine to not deliver electrical stimulation therapy. If the tachycardia is a ventricular tachycardia, one or more of the devices of system 700 may additionally determine whether the rate of the tachycardia is above a threshold and whether the cardiac electrical signal is a polymorphic signal. If the tachycardia rate is below the threshold and the cardiac electrical signal is not a polymorphic signal, one or more of the devices of system 700 may deliver, or direct a different device of system 700 to deliver, ATP therapy to the heart 710. If the tachycardia rate is above the threshold or the cardiac electrical signal is a polymorphic signal, one or more of the devices of system 700 may deliver, or direct a different device of system 700 to deliver, a defibrillation pulse to heart 710. Discriminating between such atrial and ventricular arrhythmias, and responding differently to the different types of arrhythmias, may increase the effectiveness of delivered electrical stimulation therapy and decrease negative outcomes of any delivered electrical stimulation therapy. The above description is just one example of how the disclosed systems may operate to discriminate between various arrhythmias and deliver electrical stimulation therapy in response to the different determined arrhythmias.

Figure 8:
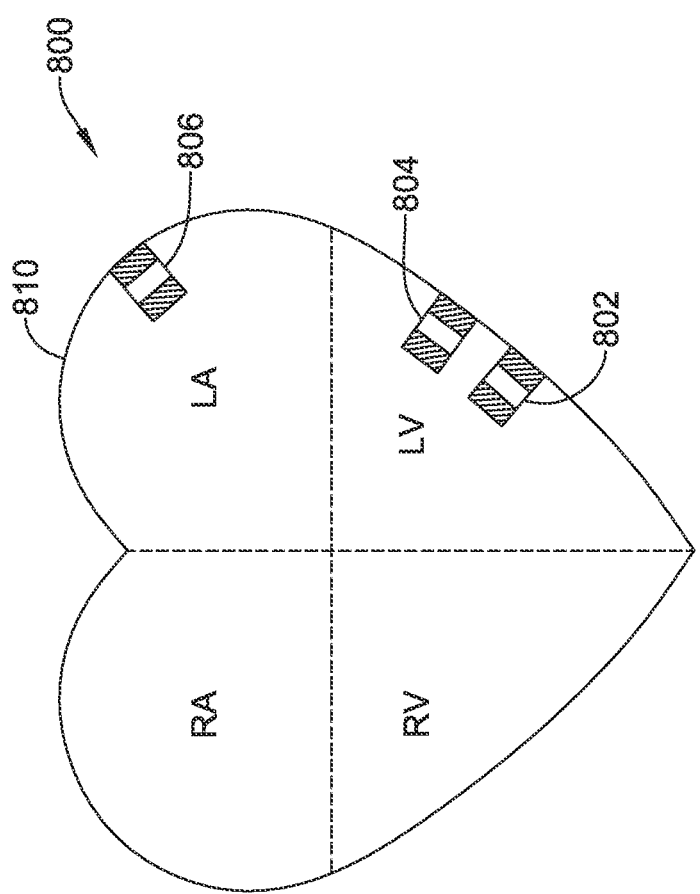
FIG. 8 is a schematic diagram illustrating a multiple leadless cardiac pacemaker (LCP) system where two LCPs are implanted within a single chamber of a heart, in accordance with yet another example of the present disclosure.
Figure 9:
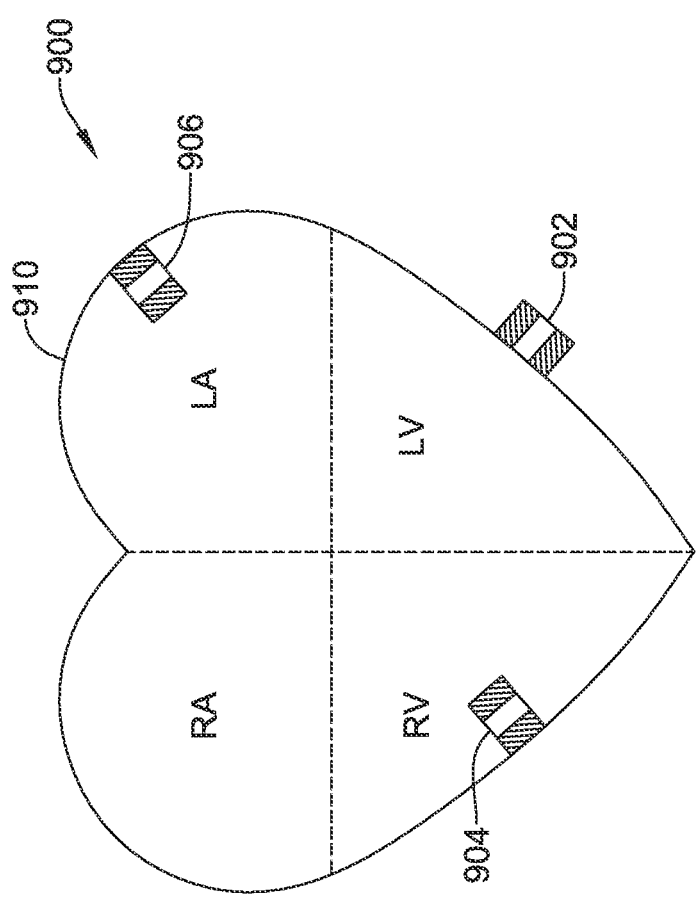
FIG. 9 is a schematic diagram illustrating a multiple leadless cardiac pacemaker (LCP) system where one of the LCPs is implanted on an epicardial surface of a heart, in accordance with another example of the present disclosure.

FIGS. 8 and 9 illustrate other example implantation locations and configurations for a multiple device medical system. For example, medical device system 800 of FIG. 8 shows three LCP devices, LCPs 802, 804, and 806. Two of the LCP devices, LCPs 802 and 804, are shown implanted within a single chamber of heart 810. In other examples, all three devices may be implanted within a single chamber of heart 810. Although two LCP's 802 and 804 are shown implanted within the LV of heart 810, in other examples, any of the chambers of heart 810 may include multiple implanted LCP devices. Implanting multiple devices within a single chamber may enhance the effectiveness of delivered electrical stimulation, as the multiple devices may increase the chances of delivering electrical stimulation therapy near a cardiac site that is an origin of an arrhythmia causing signal. As described previously with respect to the other systems, any of the other system described herein, such as systems 400 and 500 may include one or more devices implanted within a single chamber of the heart, as desired.

Medical device system 900 of FIG. 9 includes an LCP 902 implanted on an epicardial surface of heart 910. LCPs 904 and 906 are shown implanted on an endocardial surface of heart 910. In some instances, one or more additional devices of system 900 may be implanted on an epicardial surface. In some instance, a device implanted on an epicardial surface of a heart may sense intrinsic cardiac electrical signals and/or deliver appropriate electrical stimulation therapy to the heart. Accordingly, any of the systems described herein may include one or more devices implanted on an endocardial surface of a heart, as desired.

Figure 10:
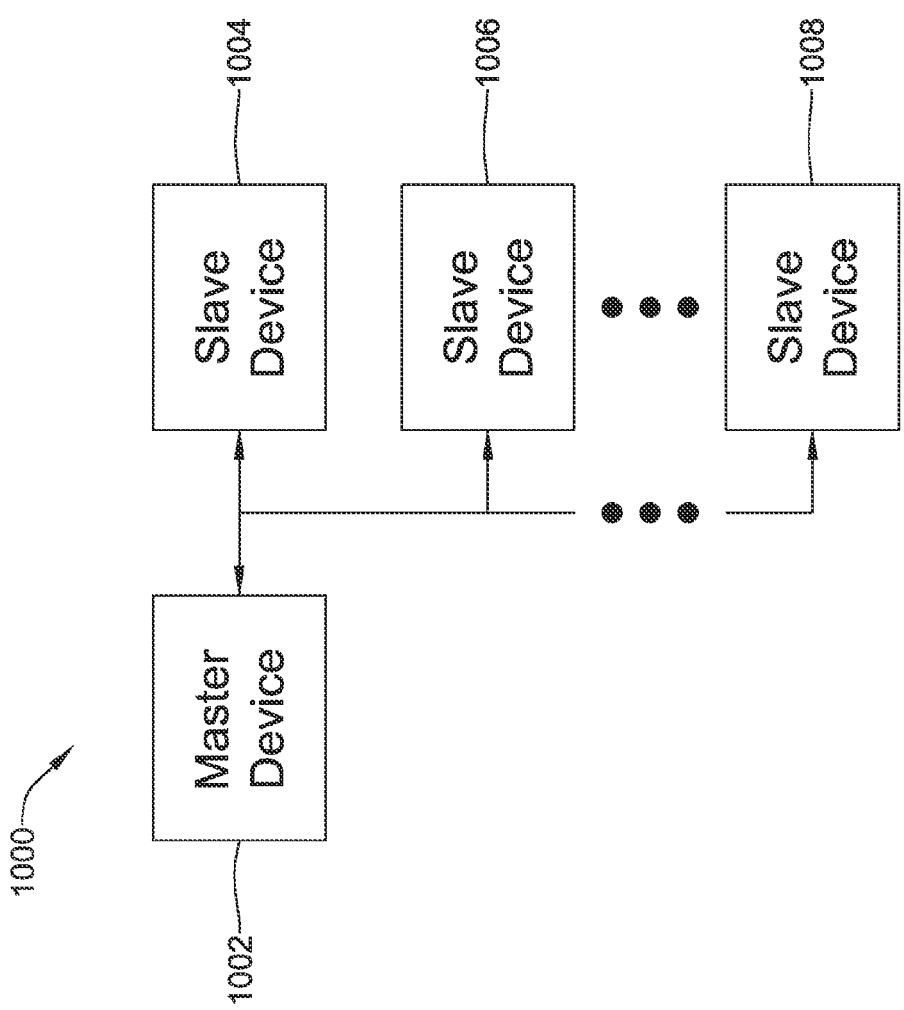
FIG. 10 is a block diagram of an exemplary medical system including a master device and multiple slave devices.
Figure 11:
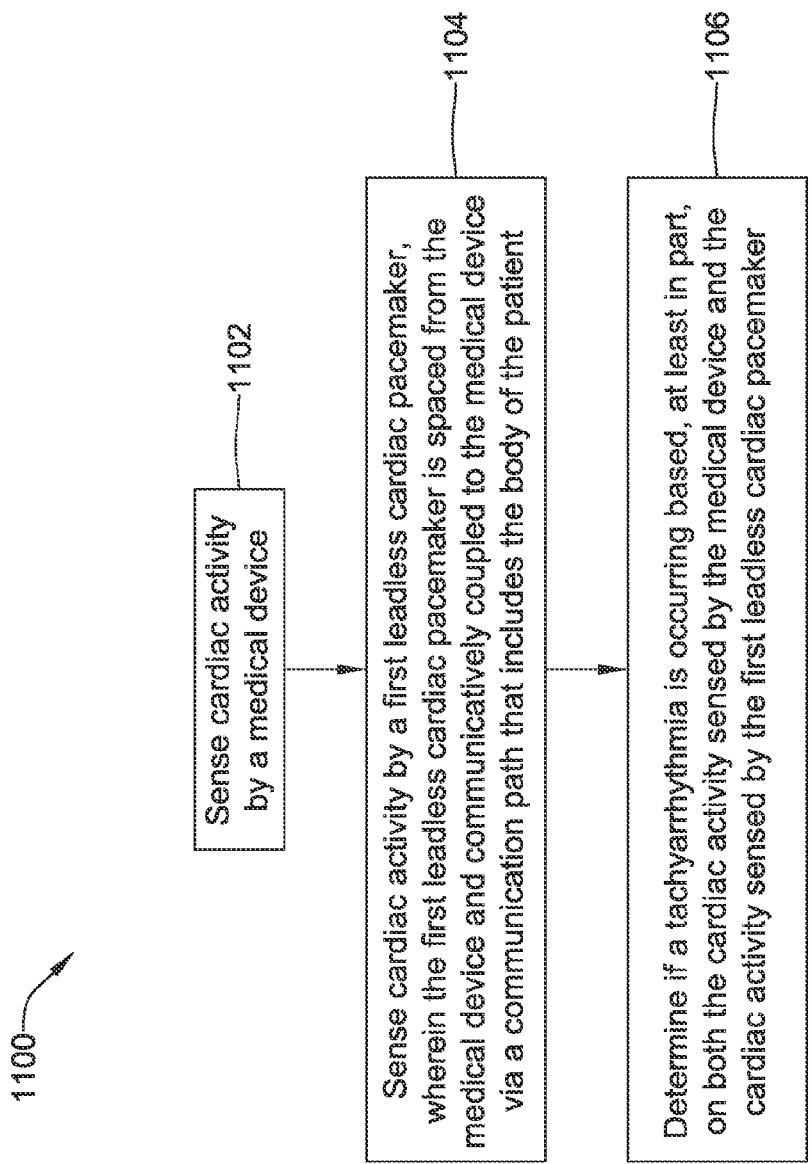
FIGS. 11-23 are flow diagrams of various illustrative methods that may be implemented by a medical device system, such as those medical device systems described with respect to FIGS. 3-10.

As noted above, in some embodiments, one device in a medical system may act a master device and the other devices may act as slave devices. FIG. 10 is a block diagram of an illustrative medical device system 1000 that includes a master device 1002 and multiple slave devices 1004, 1006, and 1008. In the example shown, the master device 1002 may conductively communicate with the slave devices 1004, 1006, and 1008 through the body of the patient. In other examples, the master and slave devices may communicate via a different communication mechanism, such as through radiofrequency (RF) signals, inductive coupling, optical signals, acoustic signals, or any other suitable for communication mechanism, as desired.

In one example, the master device 1002 may be an ICD device, for example, an ICD or an S-ICD, and may be configured to receive cardiac information from one or more slave devices 1004, 1006, and 1008. In some cases, the slave devices may be LCP's. The communicated cardiac information may include, for example, cardiac electrical signals sensed by the slave devices 1004, 1006, and 1008, preliminary determinations made by the slave devices 1004, 1006, and 1008, or other information sensed or determined by the slave devices 1004, 1006, and 1008. In some examples, master device 1002 may also sense cardiac activity. In such examples, master device 1002 may determine occurrences of arrhythmias based on either its own sensed cardiac activity and/or the received cardiac activity from the slave devices 1004, 1006 and 1008. In some instances, master device 1002 may determine that the cardiac activity from one or multiple devices of system 1000 indicates an occurrence of an arrhythmia. In some cases, although multiple devices of system 1000 may each be sensing cardiac activity, only a single device, such as master device 1002, may make the determination that a cardiac arrhythmia is occurring and that an appropriate electrical stimulation therapy is desired.

In response to determining an occurrence of an arrhythmia, master device 1002 may determine to deliver electrical stimulation therapy. In one example, master device 1002 may determine an appropriate electrical stimulation therapy based on the type of arrhythmia. Additionally, master device 1002 may determine which device or devices should deliver the electrical stimulation therapy. Master device 1002 may direct one or more of the devices, which might include the master device itself, to actually deliver the desired electrical stimulation therapy. Master device 1002 may operate according to any of the previously disclosed techniques. For example, master device 1002 may determine one or more provisional determinations of occurrences of arrhythmias before determining an actual occurrence of an arrhythmia. Master device 1002 may additionally distinguish between atrial and ventricular arrhythmias and determine appropriate electrical stimulation therapy to deliver based on the determined type of arrhythmia. In some examples, master device 1002 may determine which device or devices need to deliver electrical stimulation therapy based on which device or devices sensed the cardiac depolarization wave first of a cardiac cycle.

In some instances, multiple devices of system 1000 may determine occurrences of arrhythmias. For example, slave devices 1004, 1006, and 1008 may each determine occurrences of arrhythmias and may communicate such determinations to master device 1002. In some examples, such determinations may be considered actual or provisional determinations. Based on such received determinations, master device 1002 may determine an occurrence of an arrhythmia, in accordance with any of the previously disclosed techniques. Based on an determination of an arrhythmia, master device 1002 may deliver, and/or direct one or more of slave devices 1004, 1006, and 1008 to deliver, appropriate electrical stimulation therapy.

In some cases, not all of master device 1002 and slave devices 1004, 1006, and 1008 may be actively sensing for an arrhythmia. For instance, as described previously, in some examples only a single, or less than all of master device 1002 and slave devices 1004, 1006, and 1008, may be actively sensing for an arrhythmia. In at least one example, the actively sensing device may be sending cardiac activity to master device 1002. Based on the received cardiac activity, master device 1002 may determine an occurrence of an arrhythmia. After determining an occurrence of an arrhythmia, master device 1002 may direct a second device of system 1000 to begin actively sensing cardiac activity. This second device may additionally communicate sensed cardiac activity to master device 1002. Again, master device 1002 may determine an occurrence of an arrhythmia based on the received cardiac activity from the second device. After making one or more determinations of an occurrence of an arrhythmia, master device 1002 may deliver, or direct one or more of slave devices 1004, 1006, and 1008 to deliver, appropriate electrical stimulation therapy. In other examples, instead of sending sensed cardiac data, the devices may send determinations of occurrences of an arrhythmia to master device 1002. In some cases, master device 1002 may not sense cardiac activity. Rather, master device 1002 may make determinations of occurrences of cardiac arrhythmias based on received cardiac activity and/or determinations from those slave devices that are sensing cardiac activity.

In some cases, master device 1002 may be an LCP device, an external cardioverter-defibrillator, ICP, or diagnostic-only device. In some examples, master device 1002 and the slave devices 1004, 1006, and 1008 may have similar hardware configuration; however, they may have different software installed. In some examples, the slave devices 1004, 1006, and 1008 may be set to a "slave mode" while master device 1002 may be set to a "master mode", even though all devices share the same hardware and software features. Additionally, in some examples, the devices of system 1000 may switch between being configured as a master device and a slave device. For example, an external programmer may connect to any of the devices of such systems and alter the programming of any of the devices of the system, as desired.

FIGS. 11-22 are flow diagrams showing various methods that can be implemented by exemplary medical systems described above, for example, systems 400, 500, 600, 700, or any other exemplary medical systems described herein. Such exemplary systems may include any of MD 100 and/or LCP 200 of FIGS. 1 and 2 or any of the other devices described herein. In particular, the methods illustrated may help identify and treat arrhythmias and/or other conditions of a patient In an illustrative method 1100 of FIG. 11, a device of a medical device system may sense cardiac activity of the heart, as shown at 1102. The medical device may be an ICD, S-ICD, LCP, a diagnostic only device, or any other device as desired. The illustrative method may include sensing cardiac activity of the heart using a first leadless cardiac pacemaker (LCP), the first leadless cardiac pacemaker may be spaced from the medical device while being coupled to the medical device via a communication pathway, as shown at 1104. The communication pathway may be, for example, any of those described with respect to FIG. 3. In at least some examples, the communication pathway may pass through at least a portion of the body of the patient. One or more devices of the system may determine an occurrence of a tachyarrhythmia based, at least in part, on the cardiac activity sensed by the medical device and the first leadless cardiac pacemaker, as shown at 1106. The determination of an occurrence of a tachycardia may be made based on either the individual cardiac activity sensed by the medical device or by the first leadless cardiac pacemaker, or the combination of the sensed cardiac activity of the two devices. In some examples, the cardiac information may include both sensed cardiac electrical signals and information from other devices such as accelerometers, heart sound sensors, blood pressure sensor, blood-oxygen sensors, and the like.

In some cases, the first LCP may make a provisional determination of the occurrence of a tachycardia based on the cardiac activity sensed by the first LCP. The first LCP may send the provisional determination to the medical device. The medical device may independently make a provisional determination of the occurrence of a tachycardia based on the cardiac activity sensed by the medical device. A determination of the occurrence of a tachycardia may then be based on the provisional determination made by the first LCP and the medical device.

In some instances, the first LCP may not make a provisional determination of the occurrence of a tachycardia, but rather may send the cardiac activity sensed by the first LCP to the medical device. The medical device may then receive the cardiac activity sensed by the first LCP, and may determine the occurrence of a tachycardia based on the cardiac activity sensed by the first LCP and the cardiac activity sensed by the medical device.

Figure 12:
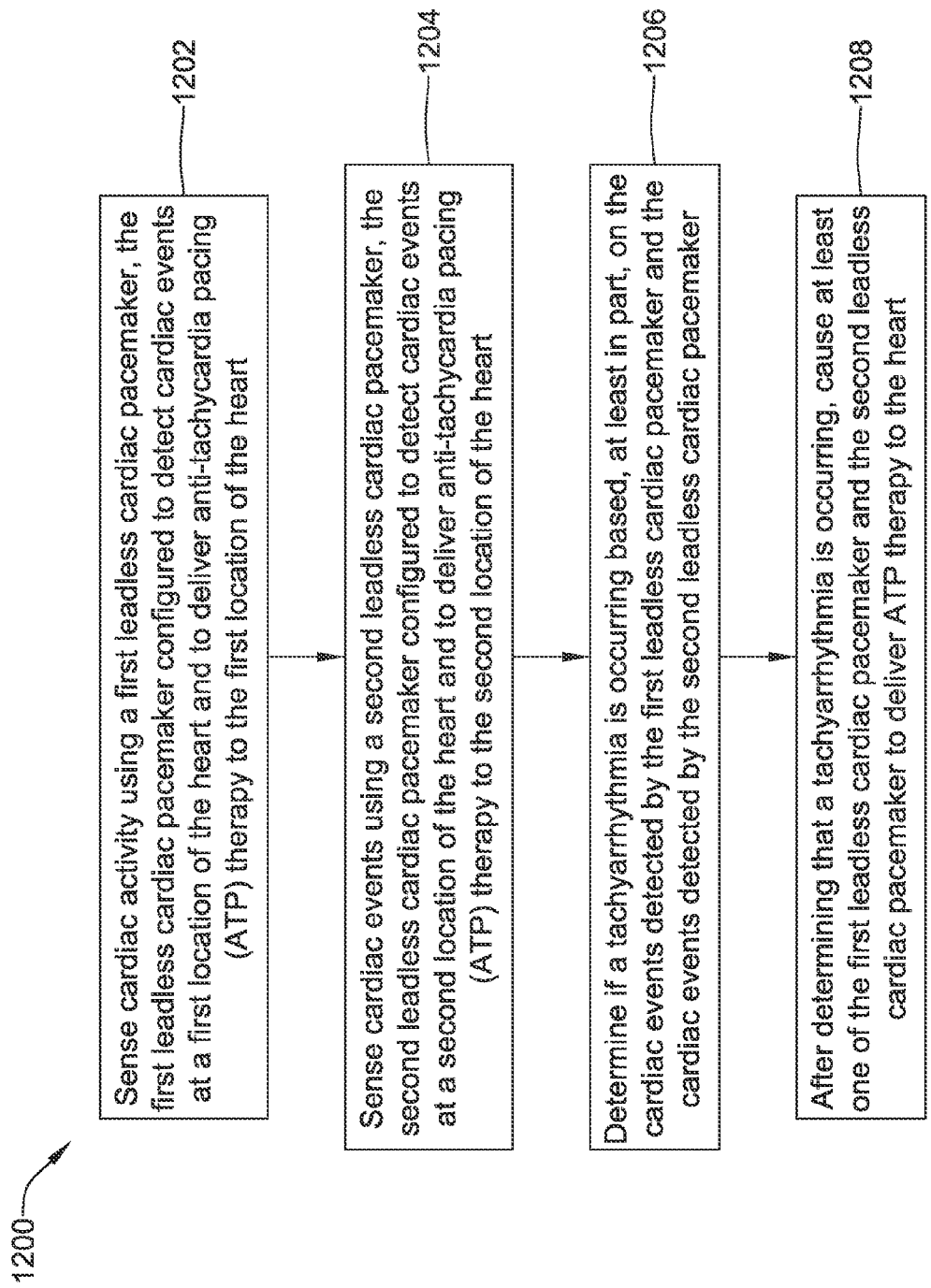

In another illustrative method 1200, as shown in FIG. 12, two or more LCPs can autonomously identify tachycardia episodes and deliver ATP. In particular, an exemplary system, such as any of those described herein, may sense cardiac activity of the heart using a first leadless cardiac pacemaker (LCP), wherein the first leadless cardiac pacemaker is configured to detect cardiac events at a first location of the heart and to deliver ATP therapy to the first location, as shown at 1202. Additionally, a second leadless cardiac pacemaker (LCP) may be configured to detect cardiac events at a second location of the heart and to deliver ATP therapy to the second location of the heart, as shown at 1204. One or more of the first and second LCPs may be configured to determine an occurrence of a tachyarrhythmia based, at least in part, on the cardiac events detected by the first leadless cardiac pacemaker and/or the cardiac events detected by the second leadless cardiac pacemaker, as shown at 1206. Once one or more of the LCPs determines an occurrence of a tachyarrhythmia, at least one of the first and the second leadless cardiac pacemaker may deliver ATP therapy to the heart, as shown at 1208.

In at least one example, the first leadless cardiac pacemaker may act as a master and the second leadless cardiac pacemaker may act as a slave. In such scenario, the first leadless cardiac pacemaker may make a determination of a tachyarrhythmia and cause the first LCP, second LCP, or both to deliver ATP therapy to the heart. In another example, the first and the second leadless cardiac pacemaker together may determine an occurrence of a tachyarrhythmia and both the first and second leadless cardiac pacemakers may deliver the ATP therapy to the heart.

Figure 13:
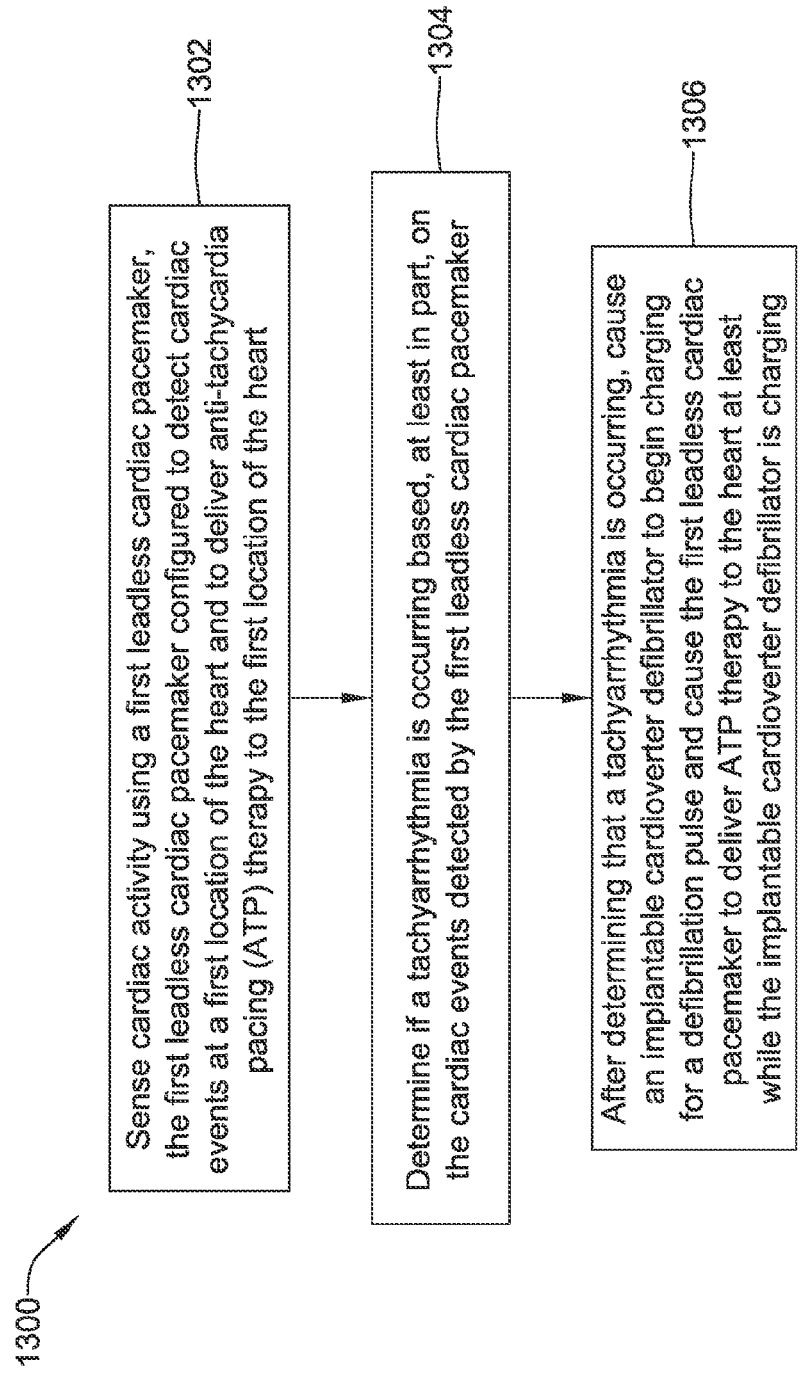

In another illustrative method 1300, as shown in FIG. 13, a medical device system, such as system 400, 500, 600, or any other medical device system described herein may include a leadless cardiac pacemaker (LCP) that may be triggered by an external device (e.g. a device external to the LCP) such as an implantable cardioverter defibrillator (ICD) or subcutaneous-ICD (S-ICD) to deliver an ATP therapy. The system may include sensing of the cardiac activity of the heart using a first leadless cardiac pacemaker (LCP), where the first leadless cardiac pacemaker may be configured to detect cardiac events at a first location of the heart and may also be configured to deliver ATP therapy to that location, as shown at 1302. Based at least in part on the cardiac events detected by the first leadless cardiac pacemaker, one or more devices of the system may determine an occurrence of a tachyarrhythmia, as shown at 1304. Once one or more of the devices have determined an occurrence of a tachyarrhythmia, an ICD or S-ICD of the system may begin charging for a defibrillation pulse, and also may instruct the first leadless cardiac pacemaker to deliver ATP therapy to the heart, as shown at 1306. The first leadless cardiac pacemaker may deliver the ATP therapy to the heart at least while the ICD or S-ICD is charging for a defibrillation pulse. If one or more of the devices subsequently determines that the ATP therapy was successful in terminating the tachyarrhythmia, the ICD or S-ICD may subsequently discharge the charged energy without delivering the defibrillation pulse. Otherwise, the ICD or S-ICD may deliver the defibrillation pulse once the ICD or S-ICD is fully charged and ready to deliver the defibrillation pulse.

Generally, one or more episodes of ventricular tachyarrhythmia in a patient may be followed by a ventricular fibrillation episode. A medical system including one or more LCPs and an ICD may be useful in treating a scenario of overlapping tachyarrhythmia and fibrillation episodes more effectively than systems that do not include both such devices.

Figure 14:
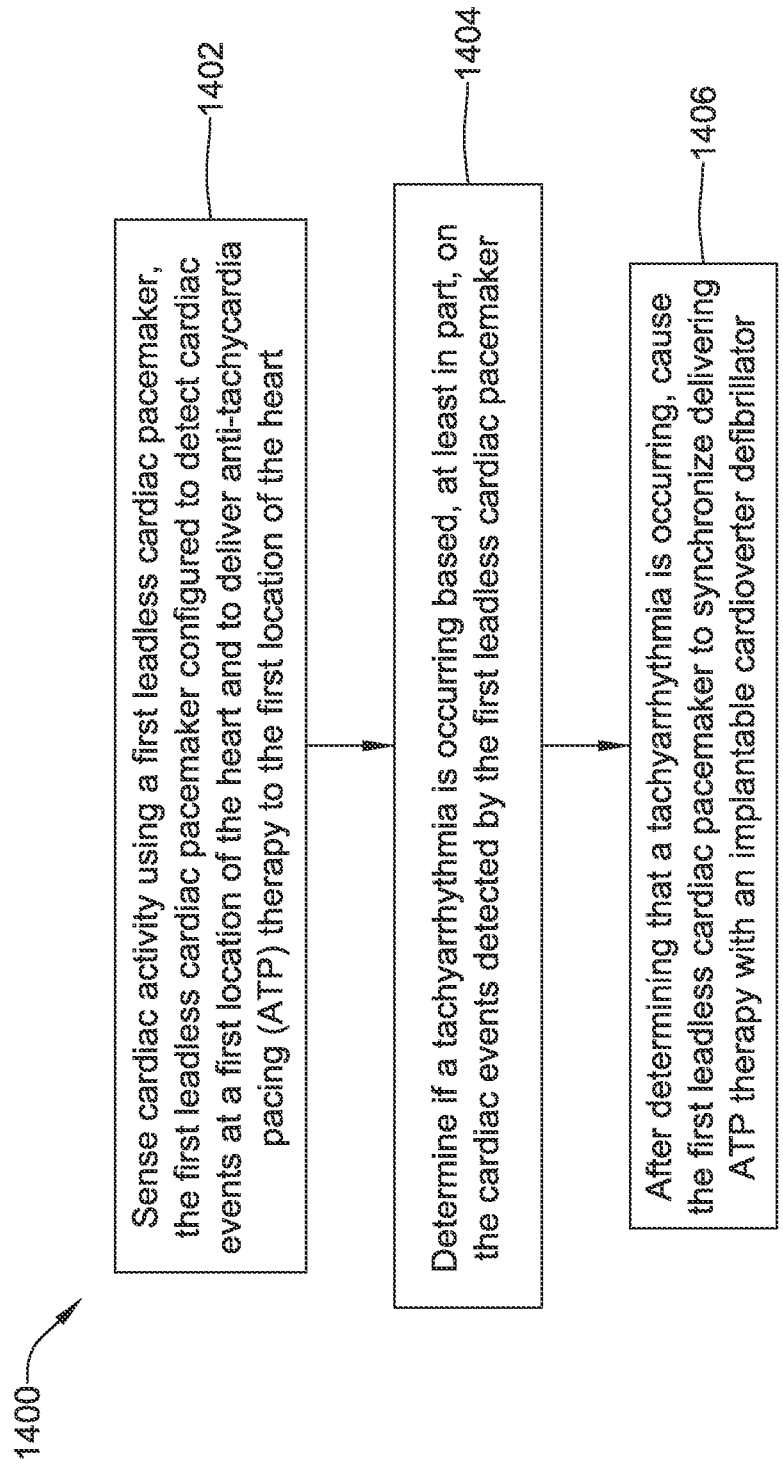

The illustrative method 1400, shown in FIG. 14, may be implemented by any system described herein that includes both an LCP device and an implantable cardioverter-defibrillator device. Illustrative method 1400 may include delivering an ATP therapy that may be synchronized between a leadless cardiac pacemaker and an implantable cardioverter defibrillator. As a first step of this illustrative method, cardiac activity of the heart may be sensed by a first leadless cardiac pacemaker (LCP), which may be configured to detect cardiac events at a first location of the heart and is further configured to deliver (ATP) therapy to that first location, as shown at 1402. One or more devices of the system may further determine an occurrence of a tachyarrhythmia based on, either partially or completely, the cardiac events detected by the first leadless cardiac pacemaker, as shown at 1404. In some examples, this may be done by comparing the cardiac activity detected by the first leadless cardiac pacemaker to a threshold cardiac activity of a normal patient or of a normal rhythm of the present patient. After determining an occurrence of a tachyarrhythmia, one or more devices of the system may cause the first leadless cardiac pacemaker to deliver ATP therapy, sometimes synchronously with ATP therapy delivered with an external device, such as the ICD (1406).

Figure 15:
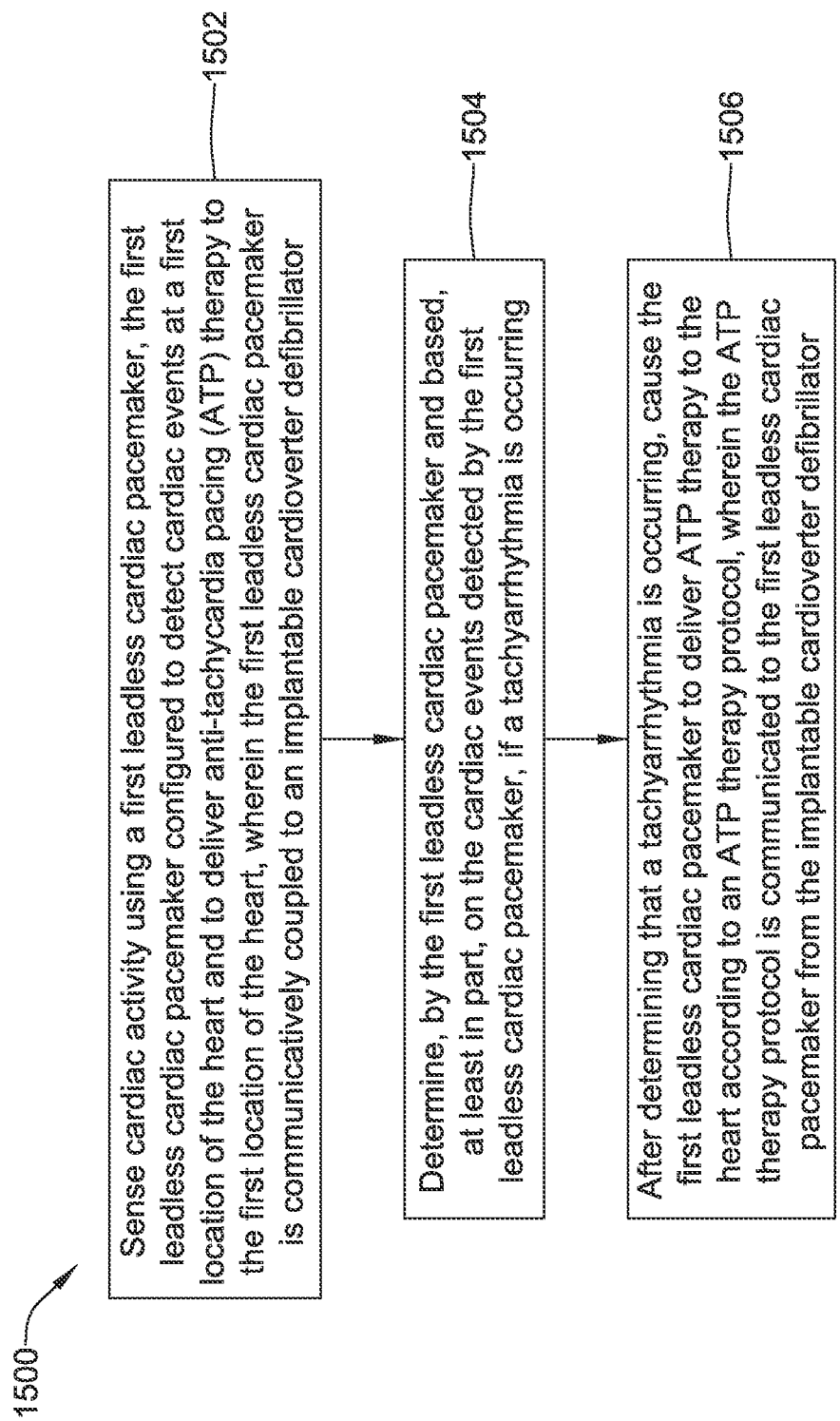

FIG. 15 includes an illustrative method 1500 that may be implemented by a system that includes an LCP and an ICD. Such system can include a first leadless cardiac pacemaker (LCP) that can sense cardiac activity and which may be communicatively coupled to an ICD, as shown at 1502. In some cases, the first leadless cardiac pacemaker may be configured to detect cardiac events at a first location of the heart and may be configured to deliver ATP therapy to the first location. One or more devices of the system may determine an occurrence of a tachyarrhythmia based on the cardiac events detected by the first leadless cardiac pacemaker, as shown at 1504. Once one or more of the devices of the system determined an occurrence of a tachyarrhythmia, the first leadless cardiac pacemaker may deliver ATP therapy to the heart based on an ATP therapy protocol, as shown at 1506. In some examples, the particular ATP therapy protocol may be communicated to the first leadless cardiac pacemaker from the ICD. In some instances, the ICD may act as a master device that can dictate the electrical impulses that are to be delivered to the first location of the heart.

Figure 16:
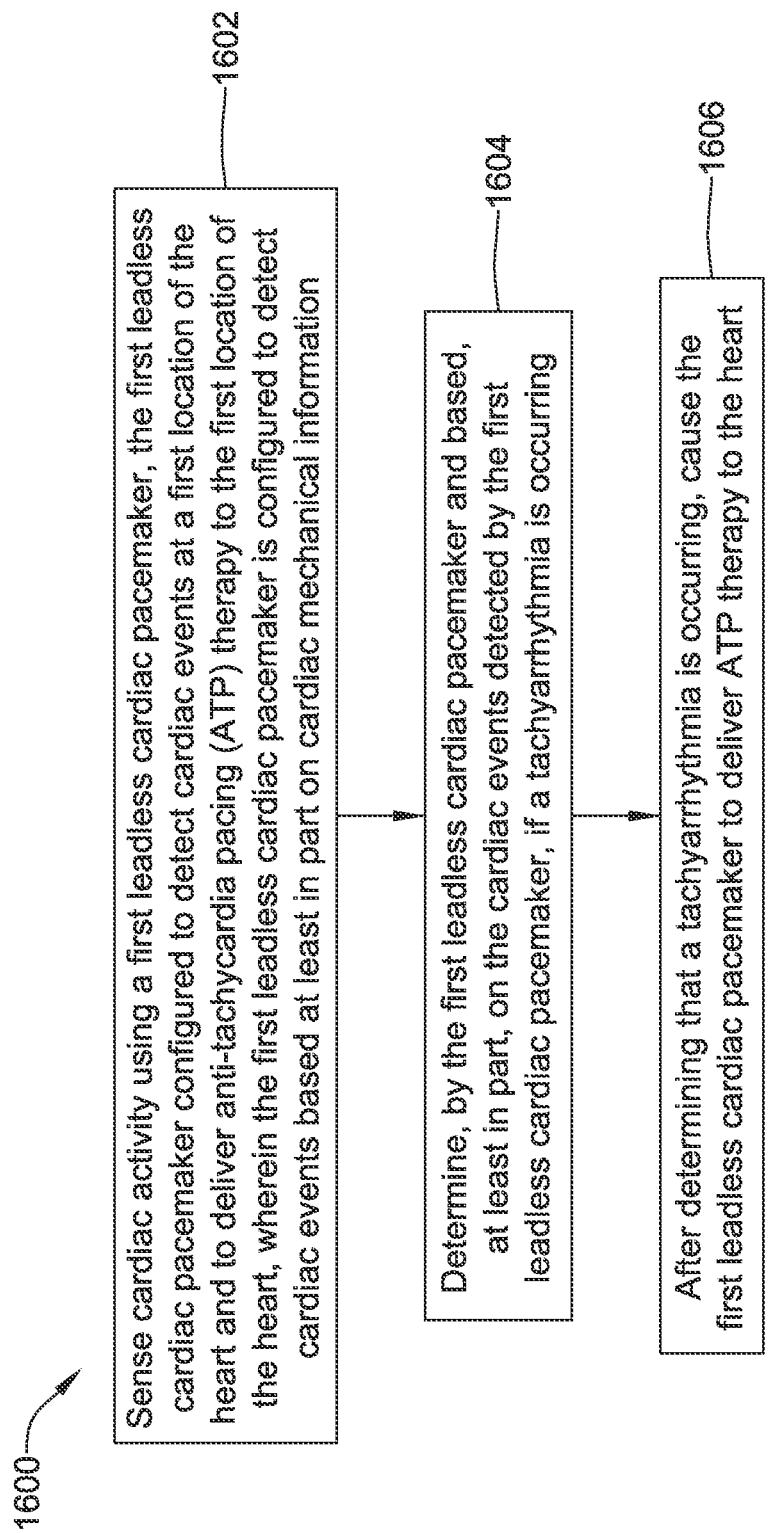

FIG. 16 discloses another illustrative method 1600 which may be implemented by a system that includes an LCP device and an ICD device. Such system may sense the cardiac activity using a first leadless cardiac pacemaker (LCP) that may be configured to detect one or more cardiac events based on, either partially or completely, cardiac mechanical information as shown at 1602. The cardiac mechanical information may include the contraction or relaxation of the cardiac muscles, such as by using an accelerometer, a heart sounds sensor, a blood pressure sensor, a blood-oxygen sensor, or any other sensor capable of sensing mechanical information of the heart. The first leadless cardiac pacemaker may be configured to detect cardiac events at a first location of the heart and can deliver ATP therapy to the first location. One or more devices of the system may further determine an occurrence of a tachyarrhythmia based, at least in part, on the cardiac events detected by the first leadless cardiac pacemaker, as shown at 1604. Once one or more devices determine an occurrence of a tachyarrhythmia, one or more devices may cause the first leadless cardiac pacemaker to deliver ATP therapy to the heart, as shown at 1606.

Figure 17:
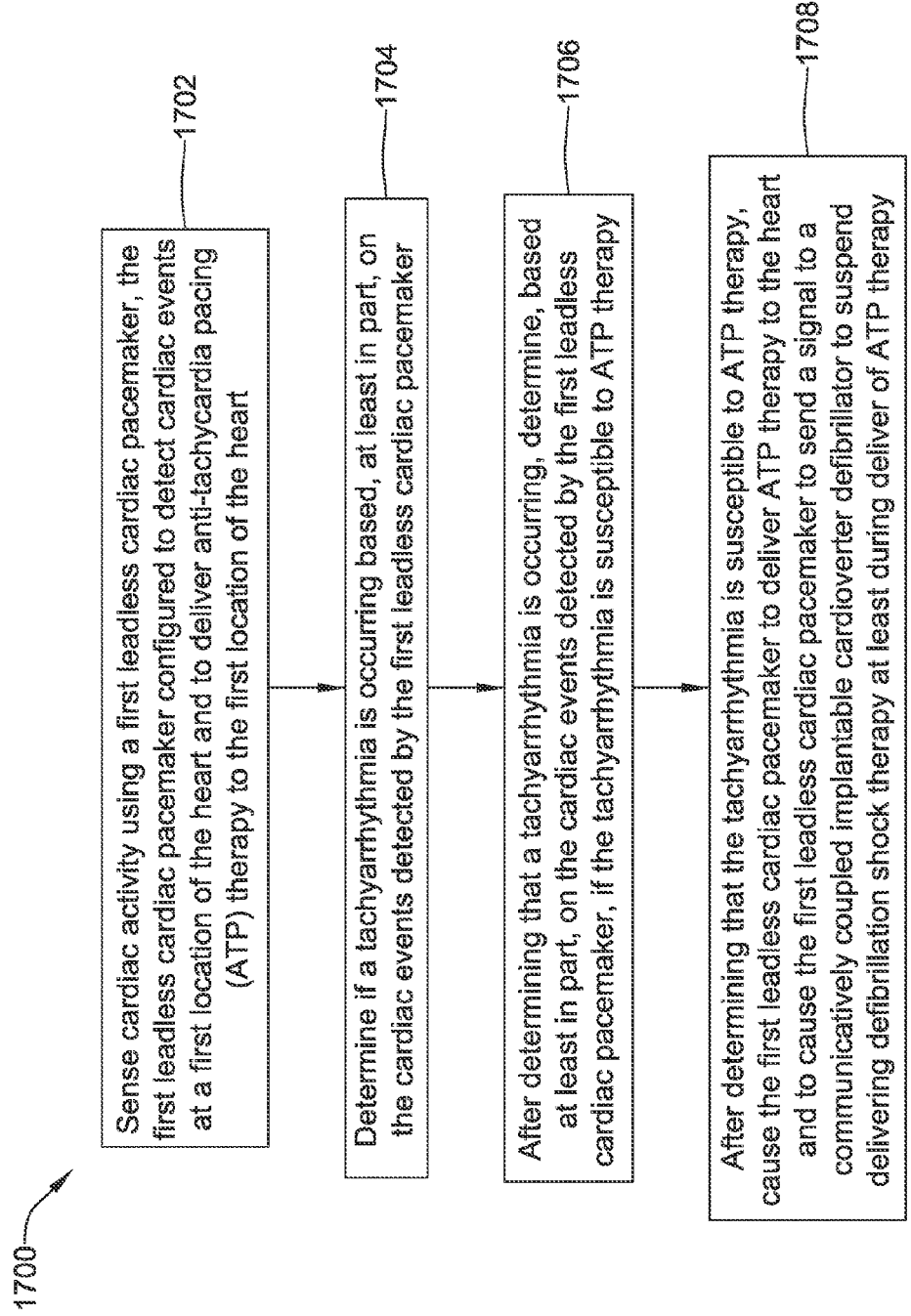

In the illustrative method 1700 shown in FIG. 17, a first leadless cardiac pacemaker (LCP) may sense cardiac activity, as shown at 1702. The first leadless cardiac pacemaker may be configured to detect cardiac events at a first location of the heart and may be configured to deliver ATP therapy to the first location. One or more devices of the system may determine an occurrence of a tachyarrhythmia based, at least in part, on the cardiac events detected by the first leadless cardiac pacemaker (1704). Once a tachyarrhythmia is identified, one or more devices of the system may determine if the tachyarrhythmia is susceptible to ATP therapy, as shown at 1706. This may be determined based, at least in part, on the cardiac events detected by the first leadless cardiac pacemaker. For example, one or more devices of the system may determine whether the tachyarrhythmia is an atrial tachyarrhythmia or a ventricular tachyarrhythmia. Additionally, one or more devices of the system may determine whether the tachycardia rate is above threshold. Some systems may further include one or more devices that determine whether the tachycardic signal is a polymorphic signal. Based on these determinations, one or more devices may determine whether the tachyarrhythmia is susceptible to ATP therapy. Once the tachyarrhythmia is determined to be susceptible to the ATP therapy, one or more devices may cause the first leadless cardiac pacemaker to deliver ATP therapy to the heart, and in some cases, may cause an implantable cardioverter defibrillator to suspend delivering defibrillation shock therapy at least during delivery of ATP therapy, as shown at 1708.

Figure 18:
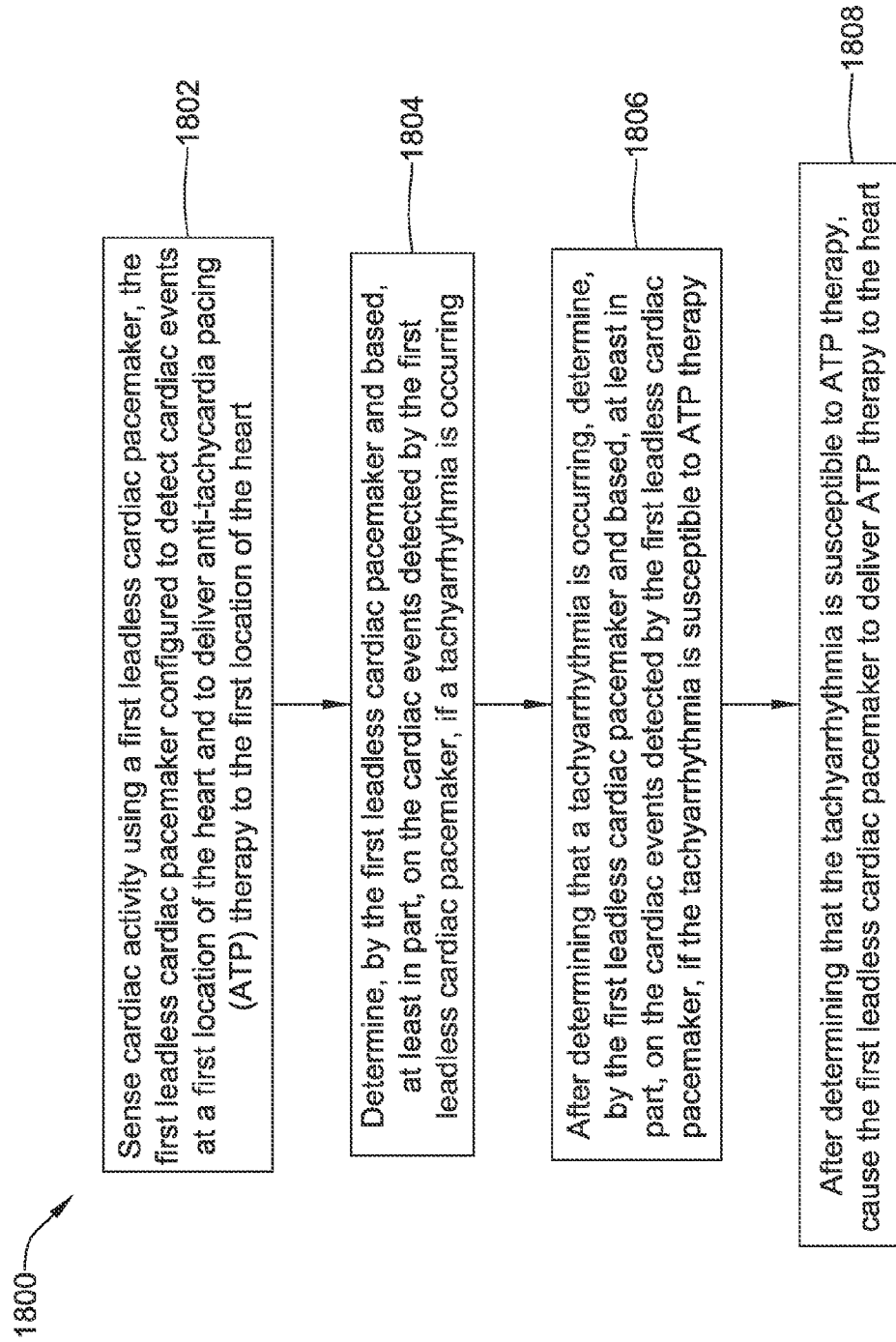

FIG. 18 describes another illustrative method 1800. A first leadless cardiac pacemaker of the system may sense cardiac activity of the heart, as shown at 1802. The first leadless cardiac pacemaker may determine an occurrence of a tachyarrhythmia, as shown at 1804. Once the first leadless cardiac pacemaker has determined an occurrence of a tachyarrhythmia, the first leadless cardiac pacemaker may determine if the tachyarrhythmia is susceptible to ATP therapy, as shown at 1806. The steps 1804 and 1806 may be completed based, at least in part, on the cardiac events detected by the first leadless cardiac pacemaker. Additionally, one or more devices of the system (which may be the first leadless cardiac pacemaker) may determine whether the tachycardic rate is above a threshold and whether the tachycardia signal is polymorphic. If a device other than the first leadless cardiac pacemaker determines one or more of these parameters, the device may in some cases communicate such parameters to the first leadless cardiac pacemaker. If the first leadless cardiac pacemaker determines that the tachyarrhythmia is susceptible to ATP therapy, the first leadless cardiac pacemaker may deliver ATP therapy to the heart, as shown at 1808. Accordingly, in such systems, an LCP device may autonomously determine an occurrence of a tachyarrhythmia and take action based on the determination.

Figure 19:
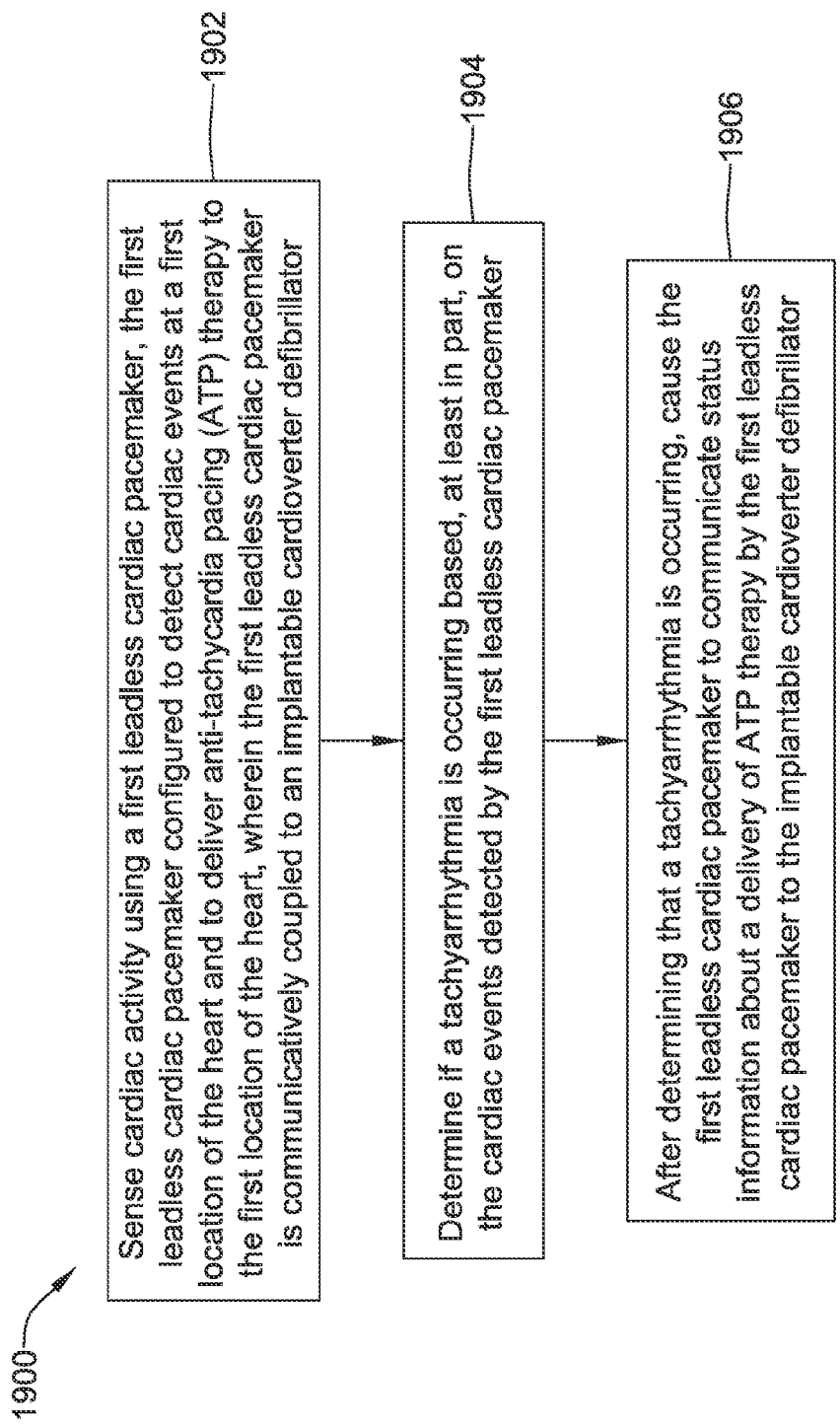

FIG. 19 shows another illustrative method 1900. In FIG. 19, a first leadless cardiac pacemaker (LCP) may be communicatively coupled to an implantable cardioverter defibrillator (ICD), as shown at 1902. The first leadless cardiac pacemaker may be configured to detect cardiac events at a first location of the heart and further configured to deliver anti-tachycardia pacing (ATP) therapy. One or more devices of the system may determine an occurrence of a tachyarrhythmia based, at least in part, on the cardiac events detected by the first leadless cardiac pacemaker, as shown at 1904. Once one or more devices of the system have determined an occurrence of a tachyarrhythmia, the first leadless cardiac pacemaker may be made to communicate status information about a delivery of ATP therapy by the first leadless cardiac pacemaker to the implantable cardioverter defibrillator (ICD), as shown at 1906. For example, the first leadless cardiac pacemaker may communicate an intent to deliver ATP therapy to the implantable cardioverter defibrillator (ICD) or that the first leadless cardiac pacemaker is currently delivering ATP therapy. In some examples, the first leadless cardiac pacemaker may communicate that the first leadless cardiac pacemaker will not deliver ATP therapy.

Figure 20:
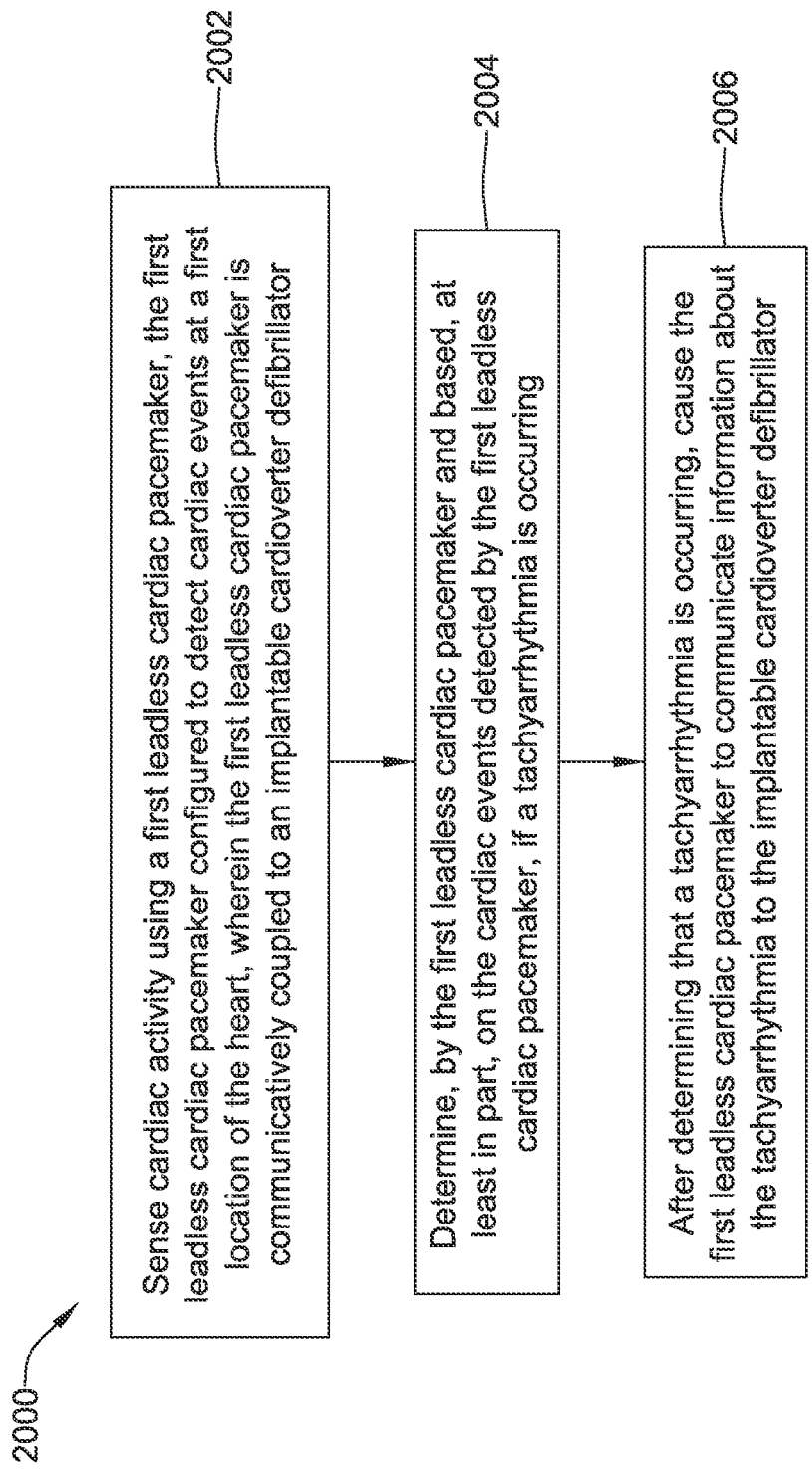

FIG. 20 shows another illustrative method 2000. In FIG. 20, a first leadless cardiac pacemaker (LCP) may be configured to detect cardiac events at a first location of the heart. One or more devices of the system may determine, based at least in part on the cardiac events detected by the first leadless cardiac pacemaker, an occurrence of a tachyarrhythmia, as shown at 2004. In a next step, the first leadless cardiac pacemaker may communicate information about the tachyarrhythmia to an implantable cardioverter defibrillator (ICD), as shown at 2006. For example, the first leadless cardiac pacemaker may communicate such information about the tachyarrhythmia such as the tachycardic rate, whether the tachycardic rate is above a threshold, and/or whether the tachycardia signal is polymorphic.

Figure 21:
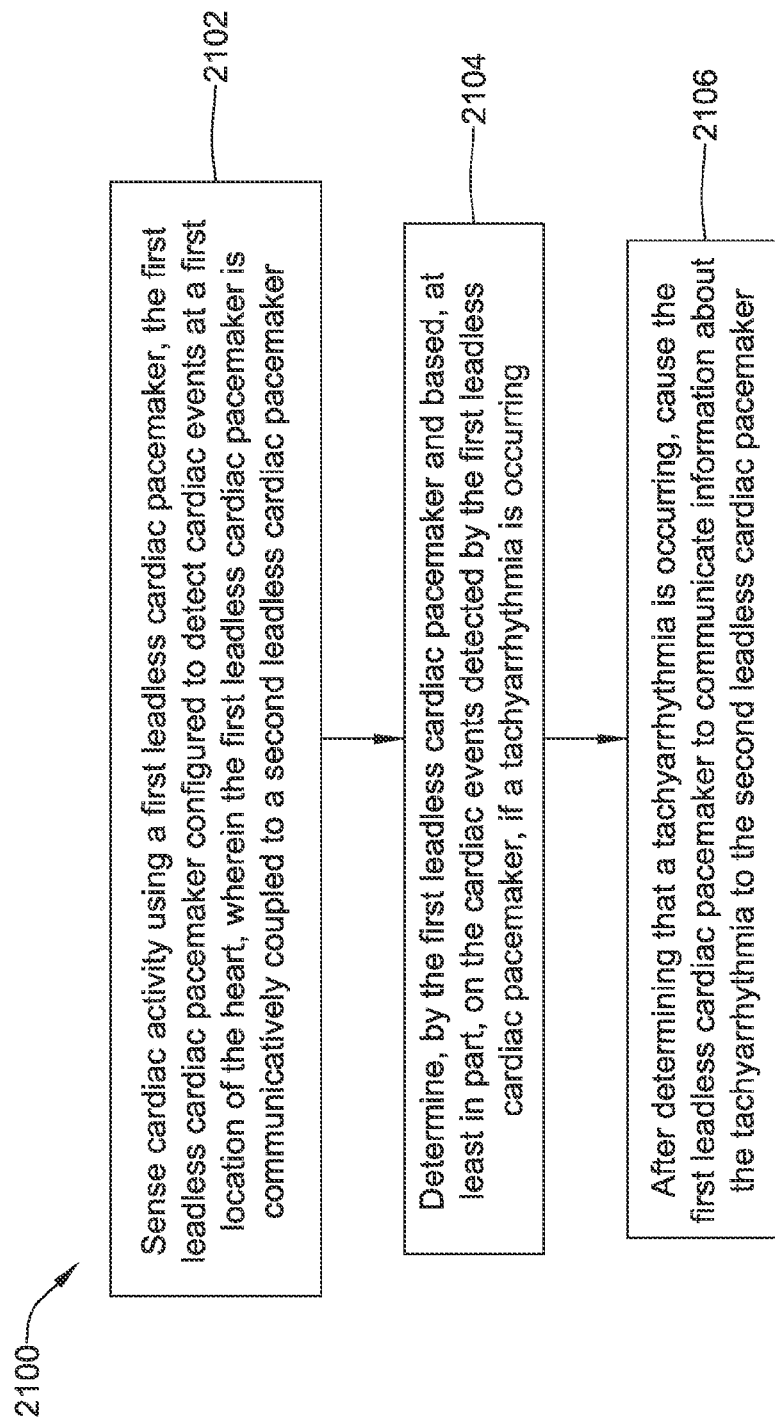

Another illustrative method 2100 is shown in FIG. 21. A first leadless cardiac pacemaker (LCP) may be configured to detect cardiac events at a first location of the heart, as shown at 2101. Based on the cardiac events detected, the first leadless cardiac pacemaker may determine an occurrence of a tachyarrhythmia, as shown at 2104. After determining an occurrence of a tachyarrhythmia, the first leadless cardiac pacemaker may communicate information about the tachyarrhythmia to a second leadless cardiac pacemaker, as shown at 2106. For example, the first leadless cardiac pacemaker may communicate information such as the tachycardic rate, whether the tachycardic rate is above a threshold, and/or whether the tachycardia signal is polymorphic.

Figure 22:
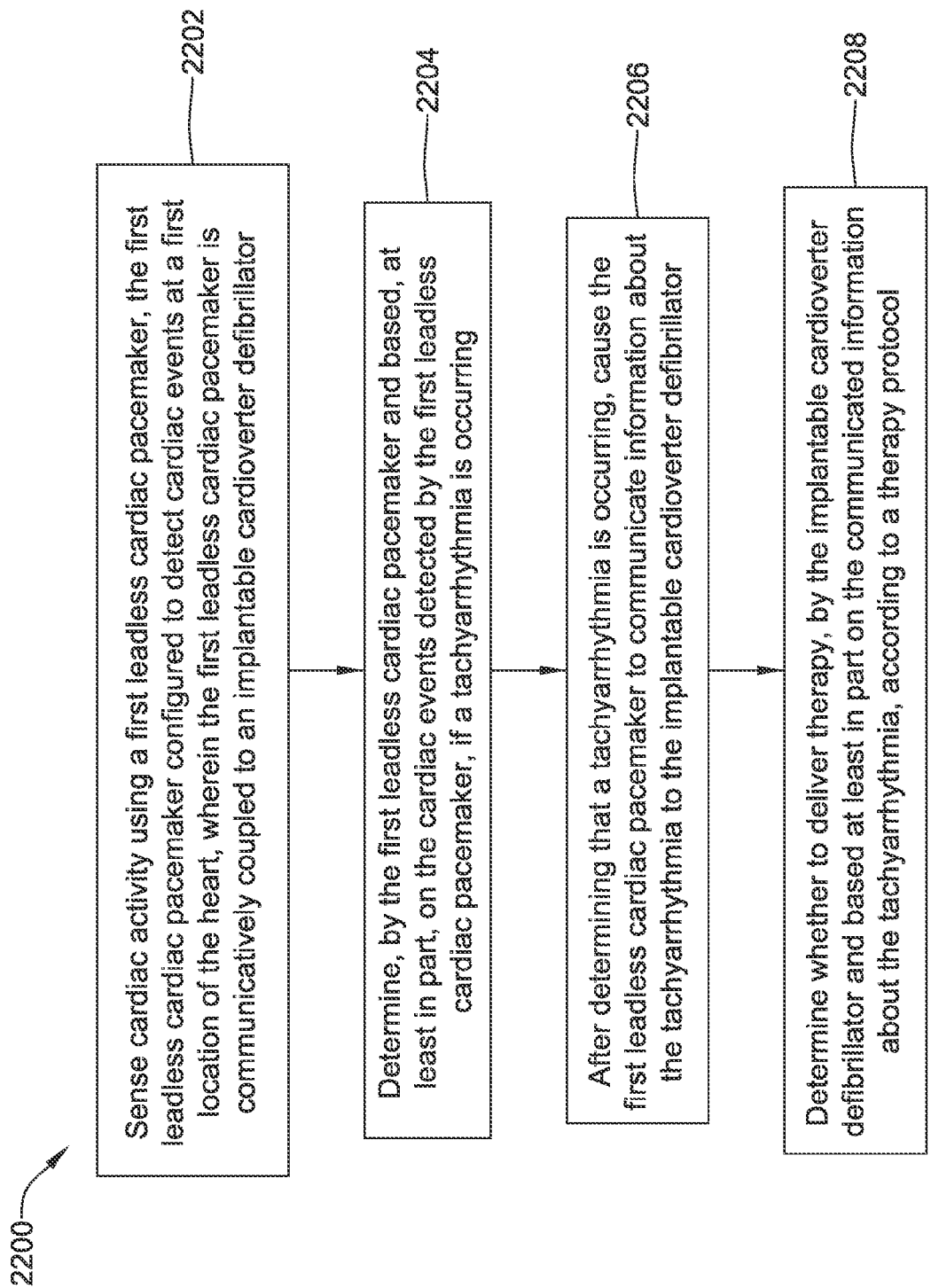

FIG. 22 shows another illustrative method 2200. A first leadless cardiac pacemaker (LCP) may be configured to detect cardiac events at a first location of the heart, as shown at 2202. The first leadless cardiac pacemaker may determine an occurrence of a tachyarrhythmia based, at least in part, on the cardiac events detected by the first leadless cardiac pacemaker, as shown at 2204. After determining an occurrence of a tachyarrhythmia, the first leadless cardiac pacemaker may communicate information about the tachyarrhythmia to an implantable cardioverter defibrillator, as shown at 2206. For example, the first leadless cardiac pacemaker may communicate information such as the tachycardic rate, whether the tachycardic rate is above a threshold, and/or whether the tachycardia signal is polymorphic. The implantable cardioverter defibrillator may determine whether to deliver therapy according to a therapy protocol, based at least in part on the communicated information about the tachyarrhythmia, as shown at 2208.

Figure 23:
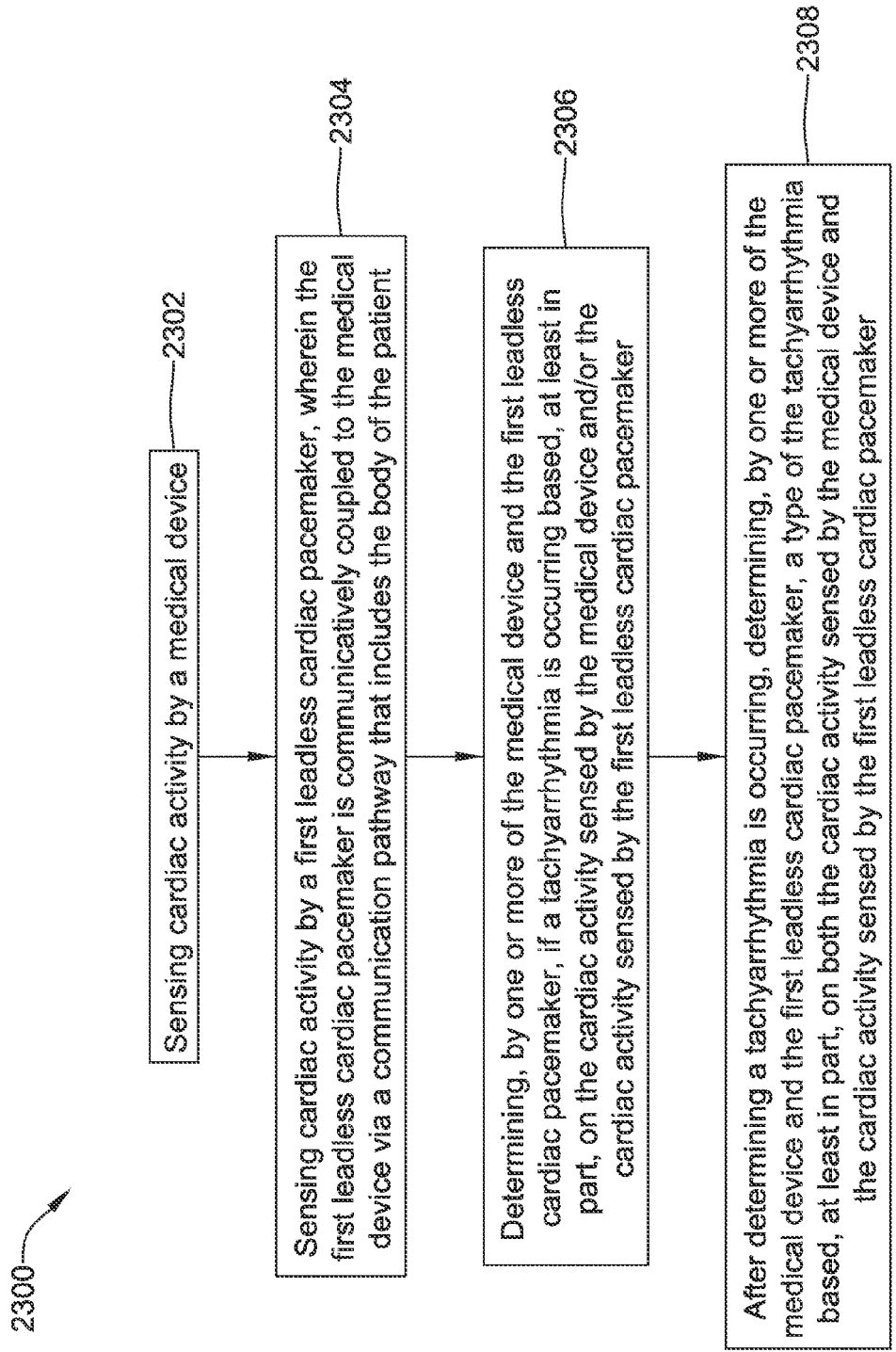

FIG. 23 shows another illustrative method 2300. Cardiac activity may be sensed by a medical device, as shown at 2302. Cardiac activity may also be sensed by a first leadless cardiac pacemaker, wherein the first leadless cardiac pacemaker is communicatively coupled to the medical device, sometimes via a communication pathway that includes the body of the patient, as shown at 2304. One or more of the medical device and the first leadless cardiac pacemaker may then determine if a tachyarrhythmia is occurring based, at least in part, on the cardiac activity sensed by the medical device and/or the cardiac activity sensed by the first leadless cardiac pacemaker, as shown at 2306. After determining that a tachyarrhythmia is occurring, one or more of the medical device and the first leadless cardiac pacemaker may determine a type of the tachyarrhythmia based, at least in part, on both the cardiac activity sensed by the medical device and the cardiac activity sensed by the first leadless cardiac pacemaker, as shown at 2308. In this example method, the cardiac activity sensed by the first leadless cardiac pacemaker may help discriminate between types of arrhythmia. In this example, the method device may include an ICD, a SICD, another leadless cardiac pacemaker, or any other suitable device.

In some instances, cardiac activity may also be sensed by a second leadless cardiac pacemaker. In some cases, one or more of the medical device, the first leadless cardiac pacemaker, and the second leadless cardiac pacemaker may determine if a tachyarrhythmia is occurring based, at least in part, on the cardiac activity sensed by the medical device, the cardiac activity sensed by the first leadless cardiac pacemaker, and/or the cardiac activity sensed by the first leadless cardiac pacemaker. After determining a tachyarrhythmia is occurring, one or more of the medical device, the first leadless cardiac pacemaker and the second leadless cardiac pacemaker may determine a type of the tachyarrhythmia based, at least in part, on the cardiac activity sensed by two or more of the medical device, the first leadless cardiac pacemaker and the second leadless cardiac pacemaker. This is another example.

Those skilled in the art will recognize that the present disclosure may be manifested in a variety of forms other than the specific embodiments described and contemplated herein. As one example, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

Additional Examples

In a first example, a method of identifying a tachyarrhythmia of a heart of a patient comprises sensing cardiac activity by a medical device, sensing cardiac activity by a first leadless cardiac pacemaker, wherein the first leadless cardiac pacemaker is spaced from the medical device and communicatively coupled to the medical device via a communication pathway that includes the body of the patient, and determining if a tachyarrhythmia is occurring based, at least in part, on both the cardiac activity sensed by the medical device and the cardiac activity sensed by the first leadless cardiac pacemaker.

In addition or alternatively, and in a second example, the medical device of the first example may comprise a second leadless cardiac pacemaker, and the second leadless cardiac pacemaker may be implanted at an atrium of the heart and the first leadless cardiac pacemaker may be implanted at a ventricle of the heart.

In addition or alternatively, and in a third example, the medical device of any of the first or second examples may comprise a second leadless cardiac pacemaker, and the second leadless cardiac pacemaker may be implanted at a left ventricle of the heart and the first leadless cardiac pacemaker may be implanted at a right ventricle of the heart.

In addition or alternatively, and in a fourth example, the medical device of any of the first through third examples may comprise a second leadless cardiac pacemaker, and the second leadless cardiac pacemaker may be implanted on an endocardial surface of the heart and the first leadless cardiac pacemaker may be implanted on an epicardial surface of the heart.

In addition or alternatively, and in a fifth example, the one of the medical device and the first leadless cardiac pacemaker of any of the first through fourth examples may perform the determining step after receiving cardiac information from the other of the medical device and the first leadless cardiac pacemaker via the communication pathway.

In addition or alternatively, and in a sixth example, the cardiac information of any of the first through fifth examples may include cardiac activity sensed by the other of the medical device and the first leadless cardiac pacemaker.

In addition or alternatively, and in a seventh example, the cardiac information of any of the first through sixth examples may include a provisional determination of tachyarrhythmia determined by the other of the medical device and the first leadless cardiac pacemaker.

In addition or alternatively, and in an eighth example, the medical device of any of the first through seventh examples may comprise one of a second leadless cardiac pacemaker, an implantable pulse generator, and a diagnostic-only medical device.

In addition or alternatively, and in a ninth example, one of the medical device and the first leadless cardiac pacemaker of any of the first though eighth examples is a master device and wherein the other of the medical device and the first leadless cardiac pacemaker is a slave device.

In addition or alternatively, and in a tenth example, any of the first through ninth examples may, upon determining an occurrence of a tachyarrhythmia, deliver anti-tachycardia pacing (ATP) therapy to the heart.

In an eleventh example, a medical system for identifying a tachyarrhythmia in a heart of a patient comprises a plurality of leadless cardiac pacemakers configured to detect cardiac activity at corresponding locations of the heart, and an Implantable Cardioverter Defibrillator (ICD) communicatively coupled to each of the plurality of leadless cardiac pacemakers via a communication pathway that includes the body of the patient, the ICD determining if a tachyarrhythmia is occurring based, at least in part, on the cardiac activity detected by two or more of the plurality of leadless cardiac pacemakers.

In addition or alternatively, and in a twelfth example, the ICD of the eleventh example may be a sub-cutaneous ICD with one or more sub-cutaneous electrodes.

In addition or alternatively, and in a thirteenth example, the cardiac activity that is detected by the two or more of the plurality of leadless cardiac pacemakers of any of the eleventh or twelfth examples may include detecting a tachyarrhythmia at the corresponding location of the heart.

In addition or alternatively, and in a fourteenth example, the ICD of any of the eleventh through thirteenth examples may determine that a tachyarrhythmia is occurring if a majority of the two or more of the plurality of leadless cardiac pacemakers determine that a tachyarrhythmia is occurring.

In addition or alternatively, and in a fifteenth example, the two or more of the plurality of leadless cardiac pacemakers of any of the eleventh through fourteenth examples may be disposed at multiple ventricular sites in the heart.

In addition or alternatively, and in a sixteenth example, the ICD of any of the eleventh through fifteenth examples may be configured to detect cardiac activity of the heart, and wherein the ICD is configured to determine if a tachyarrhythmia is occurring based, at least in part, on the cardiac activity detected by two or more of the plurality of leadless cardiac pacemakers and the cardiac activity detected by the ICD.

In addition or alternatively, and in a seventeenth example, the ICD of any of the eleventh through sixteenth examples may determine which of the plurality of leadless cardiac pacemakers deliver ATP therapy when the ICD determines that a tachyarrhythmia is occurring.

In an eighteenth example, a method of identifying a tachyarrhythmia of a heart of a patient comprises sensing cardiac activity by a medical device, sensing cardiac activity by a first leadless cardiac pacemaker, wherein the first leadless cardiac pacemaker is communicatively coupled to the medical device via a communication pathway that includes the body of the patient, determining by one or more of the medical device and the first leadless cardiac pacemaker, if a tachyarrhythmia is occurring based, at least in part, on the cardiac activity sensed by the medical device and/or the cardiac activity sensed by the first leadless cardiac pacemaker, and after determining a tachyarrhythmia is occurring, determining, by one or more of the medical device and the first leadless cardiac pacemaker, a type of the tachyarrhythmia based, at least in part, on both the cardiac activity sensed by the medical device and the cardiac activity sensed by the first leadless cardiac pacemaker. In some instances, the type of the tachyarrhythmia comprises one of a ventricular tachyarrhythmia or an atrial tachyarrhythmia.

In addition or alternatively, and in a nineteenth example, the eighteenth example may comprise delivering a first therapy to the heart based on a determined first type of tachyarrhythmia, and delivering a second therapy to the heart based on a determined second type of tachyarrhythmia.

What is claimed is:

1. A method of identifying a tachyarrhythmia of a heart of a patient, the method comprising:
    sensing cardiac activity by a first implantable medical device;
    sensing cardiac activity by a second implantable medical device, wherein the second implantable medical device is spaced from the first implantable medical device and communicatively coupled to the first implantable medical device via conducted communication through a communication pathway that includes the body of the patient;
    communicating sensed cardiac activity by the first implantable medical device to the second implantable medical device, the communicated sensed cardiac activity including sensed cardiac activity other than a determination or provisional determination of a tachyarrhythmia; and
    determining by the second implantable medical device if a tachyarrhythmia is occurring based, at least in part, on both the cardiac activity sensed by the second implantable medical device and the cardiac activity sensed by the first implantable medical device including at least some of the communicated sensed cardiac activity other than a determination or provisional determination of a tachyarrhythmia from the first implantable medical device.

2. The method of claim 1, wherein the first implantable medical device comprises a first leadless cardiac pacemaker and the second implantable medical device comprises a second leadless cardiac pacemaker, and wherein the first leadless cardiac pacemaker is implanted at an atrium of the heart and the second leadless cardiac pacemaker is implanted at a ventricle of the heart.

3. The method of claim 1, wherein the first implantable medical device comprises a first leadless cardiac pacemaker and the second implantable medical device comprises a second leadless cardiac pacemaker, and wherein the first leadless cardiac pacemaker is implanted at a left ventricle of the heart and the second leadless cardiac pacemaker is implanted at a right ventricle of the heart.

4. The method of claim 1, wherein the first implantable medical device comprises a first leadless cardiac pacemaker and the second implantable medical device comprises a second leadless cardiac pacemaker, and wherein the second leadless cardiac pacemaker is implanted on an endocardial surface of the heart and the first leadless cardiac pacemaker is implanted on an epicardial surface of the heart.

5. The method of claim 1, wherein:
    the first implantable medical device comprises a leadless cardiac pacemaker and the second implantable medical device comprises a subcutaneous cardioverter-defibrillator (S-ICD); or the second implantable medical device comprises a leadless cardiac pacemaker and the first implantable medical device comprises a subcutaneous cardioverter-defibrillator (S-ICD).

6. The method of claim 1, wherein the communicated sensed cardiac activity other than a determination or provisional determination of a tachyarrhythmia comprises one or more sensed cardiac electrical signals and/or sensed physiological parameters.

7. The method of claim 1, wherein the communicated sensed cardiac activity further includes a provisional determination of tachyarrhythmia determined by the first implantable medical device.

8. The method of claim 1, wherein the first implantable medical device comprises one of a leadless cardiac pacemaker, an implantable pulse generator, and a diagnostic-only medical device.

9. The method of claim 1, wherein one of the first implantable medical device and the second implantable medical device is a master device and wherein the other of the first implantable medical device and the second implantable medical device is a slave device.

10. The method of claim 1, further comprising, upon determining an occurrence of a tachyarrhythmia by the second implantable nedical device, delivering anti-tachycardia pacing (ATP) therapy to the heart.

11. A medical system for identifying a tachyarrhythmia in a heart of a patient, the medical system comprising:
   a plurality of leadless cardiac pacemakers configured to detect cardiac activity at corresponding locations of the heart; and
   an Implantable Cardioverter Defibrillator (ICD) communicatively coupled to each of the plurality of leadless cardiac pacemakers via a communication pathway that includes the body of the patient, the ICD determining if a tachyarrhythmia is occurring based, at least in part, on the cardiac activity detected by two or more of the plurality of leadless cardiac pacemakers.

12. The medical system of claim 11, wherein the ICD is a sub-cutaneous ICD with one or more sub-cutaneous electrodes.

13. The medical system of claim 11, wherein the cardiac activity that is detected by the two or more of the plurality of leadless cardiac pacemakers includes detecting a tachyarrhythmia at the corresponding location of the heart.

14. The medical system of claim 13, wherein the ICD determines that a tachyarrhythmia is occurring if a majority of the two or more of the plurality of leadless cardiac pacemakers determine that a tachyarrhythmia is occurring.

15. The medical system of claim 11, wherein the two or more of the plurality of leadless cardiac pacemakers are disposed at multiple ventricular sites in the heart.

16. The medical system of claim 11, wherein the ICD is also configured to detect cardiac activity of the heart, and wherein the ICD is configured to determine if a tachyarrhythmia is occurring based, at least in part, on the cardiac activity detected by two or more of the plurality of leadless cardiac pacemakers and the cardiac activity detected by the ICD.

17. The medical system of claim 11, wherein the ICD determines which of the plurality of leadless cardiac pacemakers deliver ATP therapy when the ICD determines that a tachyarrhythmia is occurring.

18. A method of identifying a tachyarrhythmia of a heart of a patient, the method comprising:
   sensing cardiac activity by a medical device;
   sensing cardiac activity by a first leadless cardiac pacemaker, wherein the first leadless cardiac pacemaker is communicatively coupled to the medical device via a communication pathway that includes the body of the patient;
   determining, by one or more of the medical device and the first leadless cardiac pacemaker, if a tachyarrhythmia is occurring based, at least in part, on the cardiac activity sensed by the medical device and/or the cardiac activity sensed by the first leadless cardiac pacemaker; and
   after determining a tachyarrhythmia is occurring, determining, by one or more of the medical device and the first leadless cardiac pacemaker, a type of the tachyarrhythmia based, at least in part, on both the cardiac activity sensed by the medical device and the cardiac activity sensed by the first leadless cardiac pacemaker.

19. The method of claim 18, wherein a type of the tachyarrhythmia comprises one of: a ventricular tachyarrhythmia or an atrial tachyarrhythmia.

20. The method of claim 18, further comprising:
   delivering a first therapy to the heart based on a determined first type of tachyarrhythmia; and
   delivering a second therapy to the heart based on a determined second type of tachyarrhythmia.

* * * * *